(12) United States Patent
Stapleford et al.

(10) Patent No.: US 10,909,830 B1
(45) Date of Patent: Feb. 2, 2021

(54) PERSONAL EMERGENCY ALERT SYSTEM, METHOD AND DEVICE

(71) Applicant: Pica Product Development, LLC, Derry, NH (US)

(72) Inventors: Scott Stapleford, Londonderry, NH (US); Richard Shevelow, Estero, FL (US); Philip Pare, Derry, NH (US); Sandra E. Shevelow, Estero, FL (US)

(73) Assignee: PICA Product Development, LLC, Derry, NH (US)

( * ) Notice: Subject to any disclaimer, the term of this patent is extended or adjusted under 35 U.S.C. 154(b) by 13 days.

(21) Appl. No.: 16/537,522

(22) Filed: Aug. 9, 2019

Related U.S. Application Data

(63) Continuation-in-part of application No. 16/183,732, filed on Nov. 8, 2018, now Pat. No. 10,694,338.
(Continued)

(51) Int. Cl.
  *G08B 21/02* (2006.01)
  *G08B 21/04* (2006.01)
  *G08B 21/18* (2006.01)

(52) U.S. Cl.
  CPC ....... *G08B 21/023* (2013.01); *G08B 21/0269* (2013.01); *G08B 21/0283* (2013.01); *G08B 21/0469* (2013.01); *G08B 21/18* (2013.01)

(58) Field of Classification Search
  None
  See application file for complete search history.

(56) References Cited

U.S. PATENT DOCUMENTS

| | | |
|---|---|---|
| 5,671,362 A | 9/1997 | Cowe et al. |
| 6,011,967 A | 1/2000 | Wieck |

(Continued)

FOREIGN PATENT DOCUMENTS

| | | |
|---|---|---|
| CA | 2619212 A1 | 9/2008 |
| CA | 2814940 A1 | 4/2012 |

(Continued)

OTHER PUBLICATIONS

Lloret et al., "A Wireless Sensor Network Deployment for Rural and Forest Fire Detection and Verification", Sensors 2009, Oct. 30, 2009, pp. 8722-8747, vol. 9, MDPI AG, Basel, Switzerland.
(Continued)

*Primary Examiner* — Chico A Foxx

(57) ABSTRACT

A system, method and device for notifying designated recipients about a personal emergency. An individual maintains a personal emergency alert device (PEAD) in accessible proximity. The PEAD is activated by onboard or remote sensor(s) in proximity to the PEAD. The sensor(s) monitor the occurrence of an emergency activation event. PEAD includes a controller. The controller, triggered by detection of an emergency event by a sensor, activates a geolocation module to obtain geolocation information, formulates an alert message, establishes a network connection, and transmits the message with geolocation information to a personal emergency alert notification service (PEANS). PEANS responds by sending a text, email or other emergency notification to designated notification recipient(s). Once activated, PEAD periodically tracks and transmits its geolocation until it runs out of power. Alternatively, PEAD can be deactivated by sending a deactivation code to the PEANS, which in turn instructs such PEAD to deactivate.

28 Claims, 17 Drawing Sheets

Related U.S. Application Data

(60) Provisional application No. 62/716,899, filed on Aug. 9, 2018, provisional application No. 62/716,896, filed on Aug. 9, 2018, provisional application No. 62/716,901, filed on Aug. 9, 2018, provisional application No. 62/841,452, filed on May 1, 2019, provisional application No. 62/582,508, filed on Nov. 7, 2017, provisional application No. 62/752,284, filed on Oct. 29, 2018.

(56) References Cited

U.S. PATENT DOCUMENTS

| | | | |
|---|---|---|---|
| 6,281,799 B1 | 8/2001 | Lake et al. | |
| 6,291,568 B1 | 9/2001 | Lussey | |
| 6,313,748 B1 | 11/2001 | Lake | |
| 6,415,544 B1 | 7/2002 | Leyerle et al. | |
| 6,445,301 B1 | 9/2002 | Farrell et al. | |
| 6,508,031 B1 | 1/2003 | Johnson et al. | |
| 6,574,912 B1 | 6/2003 | Johnson | |
| 6,631,258 B1 * | 10/2003 | Chow | H04W 76/15 455/417 |
| 6,792,395 B2 | 9/2004 | Roberts | |
| 6,864,789 B2 * | 3/2005 | Wolfe | G08B 25/08 340/539.1 |
| 6,914,529 B2 | 7/2005 | Barber et al. | |
| 6,937,156 B2 | 8/2005 | Gardner, Jr. et al. | |
| 7,002,481 B1 | 2/2006 | Crane et al. | |
| 7,026,942 B2 | 4/2006 | Cristofori et al. | |
| 7,076,211 B2 | 7/2006 | Donner et al. | |
| 7,212,129 B2 | 5/2007 | Barber et al. | |
| 7,233,781 B2 | 6/2007 | Hunter et al. | |
| 7,260,378 B2 * | 8/2007 | Holland | G01S 19/42 455/404.2 |
| 7,262,702 B2 | 8/2007 | Barber et al. | |
| 7,313,476 B2 * | 12/2007 | Nichols | G01C 21/20 340/989 |
| 7,342,504 B2 | 3/2008 | Crane et al. | |
| 7,375,629 B1 * | 5/2008 | Moyer | G08B 21/22 340/539.13 |
| 7,412,225 B2 * | 8/2008 | Islam | H04L 12/66 455/404.1 |
| 7,453,355 B2 * | 11/2008 | Bergstrom | G01S 5/0018 340/539.13 |
| 7,616,942 B2 * | 11/2009 | Karl | G08B 27/006 455/404.1 |
| 7,626,508 B2 | 12/2009 | Kosuge et al. | |
| 7,656,300 B2 | 2/2010 | Rønnau | |
| 7,715,887 B2 | 5/2010 | Cloutier et al. | |
| 7,768,413 B2 | 8/2010 | Kosuge et al. | |
| 7,952,485 B2 | 5/2011 | Schechter et al. | |
| 7,983,654 B2 * | 7/2011 | Shelton | G08B 25/016 455/404.2 |
| 8,044,796 B1 * | 10/2011 | Carr, Sr. | G07C 9/00896 340/539.13 |
| 8,378,789 B2 | 2/2013 | Moore | |
| 8,412,147 B2 | 4/2013 | Hunter et al. | |
| 8,515,386 B2 * | 8/2013 | Hasenfang | H04M 3/42348 455/404.2 |
| 8,520,589 B2 | 8/2013 | Bhatt et al. | |
| 8,521,192 B2 * | 8/2013 | Ahlgren | H04W 64/00 455/456.6 |
| 8,599,010 B2 | 12/2013 | Bose et al. | |
| 8,646,204 B2 | 2/2014 | Chiu | |
| 8,676,377 B2 | 3/2014 | Siegel et al. | |
| 8,711,785 B2 * | 4/2014 | Gholmieh | H04L 5/0091 370/329 |
| 8,797,168 B2 | 8/2014 | Tolley et al. | |
| 8,830,071 B2 | 9/2014 | Borth et al. | |
| 9,015,987 B2 | 4/2015 | Moran et al. | |
| 9,026,147 B2 | 5/2015 | Galvin et al. | |
| 9,070,268 B2 | 6/2015 | Monacos et al. | |
| 9,159,211 B2 | 10/2015 | O'Brien et al. | |
| 9,188,679 B2 * | 11/2015 | Hamada | G01S 19/34 |
| 9,196,148 B1 | 11/2015 | Hutz | |
| 9,226,481 B1 | 1/2016 | Paripati | |
| 9,265,001 B1 | 2/2016 | Tannenbaum et al. | |
| 9,341,014 B2 | 5/2016 | Oshima et al. | |
| 9,380,775 B2 | 7/2016 | Frojmovics | |
| 9,439,412 B2 | 9/2016 | Kittelson | |
| 9,439,995 B2 | 9/2016 | Conroy et al. | |
| 9,442,594 B2 | 9/2016 | Graham et al. | |
| 9,460,448 B2 * | 10/2016 | Felgate | G08B 21/18 |
| 9,510,582 B2 | 12/2016 | David et al. | |
| 9,534,958 B1 | 1/2017 | Lhamon et al. | |
| 9,542,835 B2 | 1/2017 | Borth et al. | |
| 9,547,973 B1 | 1/2017 | Hutz | |
| 9,613,521 B2 | 4/2017 | Hunter et al. | |
| 9,652,975 B1 * | 5/2017 | Riley | G08B 25/009 |
| 9,674,652 B2 * | 6/2017 | Ranki | H01Q 21/00 |
| 9,740,921 B2 | 8/2017 | McClure et al. | |
| 9,750,239 B2 | 9/2017 | Vilinskis et al. | |
| 9,767,230 B2 | 9/2017 | Kimchi et al. | |
| 9,786,153 B2 * | 10/2017 | London | G08B 21/24 |
| 9,799,207 B1 | 10/2017 | Tavares | |
| 9,911,095 B2 | 3/2018 | Mashburn et al. | |
| 9,986,313 B2 | 5/2018 | Schwarzkopf et al. | |
| 10,026,300 B1 | 7/2018 | Hutz | |
| 10,049,341 B2 | 8/2018 | Jones et al. | |
| 10,079,903 B1 | 9/2018 | Cunico et al. | |
| 10,085,438 B1 | 10/2018 | Dismang | |
| 10,111,079 B2 * | 10/2018 | Baldree | H04M 1/7253 |
| 10,111,416 B2 | 10/2018 | Rich et al. | |
| 10,127,797 B2 * | 11/2018 | Probin | G08B 13/2491 |
| 10,152,035 B2 | 12/2018 | Reid et al. | |
| 10,157,372 B2 | 12/2018 | Brailovskiy et al. | |
| 10,169,587 B1 * | 1/2019 | Nix | H04L 9/0838 |
| 10,192,194 B2 | 1/2019 | Bernhardt et al. | |
| 10,325,241 B2 | 6/2019 | Haimi | |
| 10,489,743 B2 | 11/2019 | Aepli | |
| 2001/0033230 A1 | 10/2001 | Barber et al. | |
| 2003/0058097 A1 | 3/2003 | Saltzstein et al. | |
| 2003/0213161 A1 | 11/2003 | Gardner et al. | |
| 2004/0090329 A1 | 5/2004 | Hitt | |
| 2004/0100394 A1 | 5/2004 | Hitt | |
| 2004/0203879 A1 * | 10/2004 | Gardner | G01S 19/34 455/456.1 |
| 2005/0014482 A1 * | 1/2005 | Holland | G01S 19/48 455/404.1 |
| 2005/0151653 A1 | 7/2005 | Chan et al. | |
| 2005/0162279 A1 | 7/2005 | Marshall et al. | |
| 2006/0240853 A1 | 10/2006 | Donner et al. | |
| 2007/0030156 A1 | 2/2007 | Schlager et al. | |
| 2007/0032830 A1 * | 2/2007 | Bowers | G08B 25/016 607/5 |
| 2007/0254626 A1 * | 11/2007 | Ahlgren | G01S 19/43 455/404.2 |
| 2008/0055094 A1 | 3/2008 | Barber et al. | |
| 2008/0204253 A1 | 8/2008 | Cottee et al. | |
| 2008/0210153 A1 | 9/2008 | Alvarado | |
| 2008/0234592 A1 * | 9/2008 | Lim | A61B 5/0006 600/509 |
| 2008/0258910 A1 * | 10/2008 | Stapleford | G08B 27/001 340/540 |
| 2009/0189807 A1 * | 7/2009 | Scalisi | G01S 19/34 342/357.57 |
| 2009/0260276 A1 | 10/2009 | Kirsch et al. | |
| 2009/0315767 A1 * | 12/2009 | Scalisi | G01S 19/34 342/357.74 |
| 2010/0134301 A1 | 6/2010 | Borth et al. | |
| 2010/0148956 A1 | 6/2010 | Song et al. | |
| 2010/0176954 A1 | 7/2010 | Alvarado | |
| 2010/0283610 A1 | 11/2010 | Wetzel et al. | |
| 2011/0102257 A1 * | 5/2011 | Spyropoulos | G01S 19/34 342/357.31 |
| 2011/0109460 A1 | 5/2011 | Lloyd et al. | |
| 2011/0230160 A1 | 9/2011 | Felgate | |
| 2011/0242043 A1 | 10/2011 | Yarvis et al. | |
| 2011/0312286 A1 | 12/2011 | Lin et al. | |
| 2012/0149312 A1 * | 6/2012 | Velusamy | H04M 1/72569 455/68 |

(56) References Cited

U.S. PATENT DOCUMENTS

| | | | |
|---|---|---|---|
| 2012/0235860 A1* | 9/2012 | Ghazarian | G08B 13/1427 |
| | | | 342/357.4 |
| 2012/0245969 A1 | 9/2012 | Campbell | |
| 2013/0162443 A1 | 6/2013 | Oppenheimer et al. | |
| 2013/0208575 A1* | 8/2013 | Sammut | G04G 13/021 |
| | | | 368/250 |
| 2014/0071276 A1 | 3/2014 | Seifer et al. | |
| 2014/0085084 A1* | 3/2014 | Ghazarian | H04W 4/023 |
| | | | 340/539.13 |
| 2014/0085100 A1 | 3/2014 | Rich et al. | |
| 2014/0087762 A1 | 3/2014 | Galvin et al. | |
| 2014/0106677 A1 | 4/2014 | Altman | |
| 2014/0118135 A1 | 5/2014 | O'Brien et al. | |
| 2014/0253377 A1* | 9/2014 | Scalisi | G01S 19/49 |
| | | | 342/357.74 |
| 2014/0323079 A1* | 10/2014 | Paolini | H04W 4/90 |
| | | | 455/404.2 |
| 2015/0065167 A1* | 3/2015 | Scalisi | H04W 8/02 |
| | | | 455/456.1 |
| 2015/0120083 A1* | 4/2015 | Gurovich | G07C 5/008 |
| | | | 701/1 |
| 2015/0215732 A1* | 7/2015 | Ranki | H04W 52/0274 |
| | | | 370/328 |
| 2015/0290392 A1* | 10/2015 | Henderson | A61M 5/3204 |
| | | | 604/111 |
| 2015/0351336 A1 | 12/2015 | Gilbert et al. | |
| 2016/0018800 A1* | 1/2016 | Gettings | G08C 17/02 |
| | | | 700/19 |
| 2016/0048798 A1 | 2/2016 | Meyer et al. | |
| 2016/0086475 A1 | 3/2016 | Rich et al. | |
| 2016/0192865 A1 | 7/2016 | Datta et al. | |
| 2016/0202078 A1* | 7/2016 | Scalisi | B60K 35/00 |
| | | | 701/519 |
| 2016/0240074 A1 | 8/2016 | Probin et al. | |
| 2016/0269533 A1 | 9/2016 | Taylor et al. | |
| 2016/0371952 A1 | 12/2016 | Felgate | |
| 2016/0379176 A1 | 12/2016 | Brailovskiy et al. | |
| 2017/0035042 A1 | 2/2017 | Ben-Dashan et al. | |
| 2017/0111128 A1 | 4/2017 | Hammerschmidt et al. | |
| 2017/0112116 A1 | 4/2017 | Ji et al. | |
| 2017/0140632 A1 | 5/2017 | Klein et al. | |
| 2017/0208426 A1 | 7/2017 | Komoni et al. | |
| 2017/0215381 A1 | 8/2017 | Shen et al. | |
| 2017/0231214 A1 | 8/2017 | Vaisblat et al. | |
| 2017/0231215 A1 | 8/2017 | Barton | |
| 2017/0318796 A1 | 11/2017 | Vaisblat et al. | |
| 2017/0360026 A1 | 12/2017 | Zirkle et al. | |
| 2017/0374437 A1 | 12/2017 | Schwarzkopf et al. | |
| 2018/0006719 A1 | 1/2018 | Cress et al. | |
| 2018/0033289 A1 | 2/2018 | Lee | |
| 2018/0075596 A1 | 3/2018 | Fryshman | |
| 2018/0096581 A1 | 4/2018 | Daly, Jr. | |
| 2018/0190084 A1* | 7/2018 | Mandlakazi | G08B 5/36 |
| 2018/0199172 A1 | 7/2018 | Boily et al. | |
| 2018/0199306 A1* | 7/2018 | Edge | G01S 5/10 |
| 2018/0199565 A1 | 7/2018 | Zosimadis | |
| 2018/0217228 A1* | 8/2018 | Edge | G01S 5/0236 |
| 2018/0249696 A1 | 9/2018 | Daly, Jr. et al. | |
| 2018/0254905 A1* | 9/2018 | Chun | H04L 9/3236 |
| 2018/0279603 A1 | 10/2018 | Madl et al. | |
| 2018/0295831 A1 | 10/2018 | Reid et al. | |
| 2018/0299842 A1 | 10/2018 | Reid et al. | |
| 2018/0301918 A1* | 10/2018 | Lupo | H02J 7/00 |
| 2018/0322454 A1 | 11/2018 | Komoni | |
| 2018/0338681 A1 | 11/2018 | Scherer et al. | |
| 2018/0350227 A1 | 12/2018 | Komoni | |
| 2019/0037829 A1 | 2/2019 | Laut et al. | |
| 2019/0078930 A1 | 3/2019 | Ravulapati | |
| 2019/0096058 A1 | 3/2019 | Fryshman | |
| 2019/0111272 A1* | 4/2019 | Hochhalter | A61N 1/3904 |
| 2019/0121302 A1 | 4/2019 | Reid et al. | |
| 2019/0141295 A1 | 5/2019 | Lazar | |
| 2019/0197864 A1* | 6/2019 | Hui | G08B 21/0277 |
| 2019/0200597 A1 | 7/2019 | Borth et al. | |
| 2019/0230148 A1 | 7/2019 | Borlik | |
| 2019/0385438 A1* | 12/2019 | Cholhan | G08B 21/0453 |
| 2020/0005626 A1 | 1/2020 | Triventi et al. | |
| 2020/0029550 A1 | 1/2020 | Koziar et al. | |
| 2020/0045932 A1 | 2/2020 | Knight et al. | |
| 2020/0134812 A1 | 4/2020 | Fryshman | |

FOREIGN PATENT DOCUMENTS

| | | |
|---|---|---|
| CA | 2920216 A1 | 8/2016 |
| CN | 102413553 A | 4/2012 |
| CN | 102457932 A | 5/2012 |
| CN | 203799486 U | 8/2014 |
| CN | 105894760 A | 8/2016 |
| EP | 3059719 A1 | 8/2016 |
| EP | 3013141 B1 | 9/2019 |
| ES | 2691531 T3 | 11/2018 |
| RU | 179998 U1 | 5/2018 |
| WO | 0226033 A1 | 4/2002 |
| WO | 2002100170 A3 | 10/2003 |
| WO | 2007094974 A1 | 8/2007 |
| WO | 2008064033 A2 | 5/2008 |
| WO | 2010030346 A1 | 3/2010 |
| WO | 2017004701 A1 | 1/2017 |
| WO | 2017011916 A1 | 1/2017 |
| WO | 2017171281 A2 | 10/2017 |
| WO | 2018145880 A1 | 8/2018 |
| WO | 2019157536 A1 | 8/2019 |
| WO | 2019168855 A2 | 9/2019 |

OTHER PUBLICATIONS

Mekki et al., "A comparative study of LPWAN technologies for large-scale IoT deployment", ICT Express, Mar. 2019, pp. 1-7, vol. 5, Issue 1, Korean Institute of Communications and Information Sciences (KICS), production and hosting by Elsevier B.V., https://www.sciencedirect.com/science/article/pii/S2405959517302953?via%3Dihub.

Petric et al., "Measurements, Performance and Analysis of LoRa FABIAN, a real-world implementation of LPWAn", Personal, Indoor, and Mobile Radio Communications (PIMRC), 2016 IEEE 27th Annual International Symposium on Personal, Indoor, and Mobile Radio Communications, Sep. 2016, Valencia, Spain. , https://hal-imt.archives-ouvertes.fr/hal-01331966.

Son et al., "A Design and Implementation of Forest-Fires Surveillance System based on Wireless Sensor Networks for South Korea Mountains", International Journal of Computer Science and Network Security, Sep. 2006, pp. 124-130, vol. 6 No. 9B, IJCSNS.org, Seoul, Korea.

Tim Urban, Everything You Should Know About Sound, Wait But Why, Mar. 9, 2019, https://waitbutwhy.com/2016/03/sound.html.

Yousef et al. "A low-cost LoRaWAN testbed for IoT: Implementation and measurements." Internet of Things (WF-IoT), 2018 IEEE 4th World Forum on. IEEE, 2018.

* cited by examiner

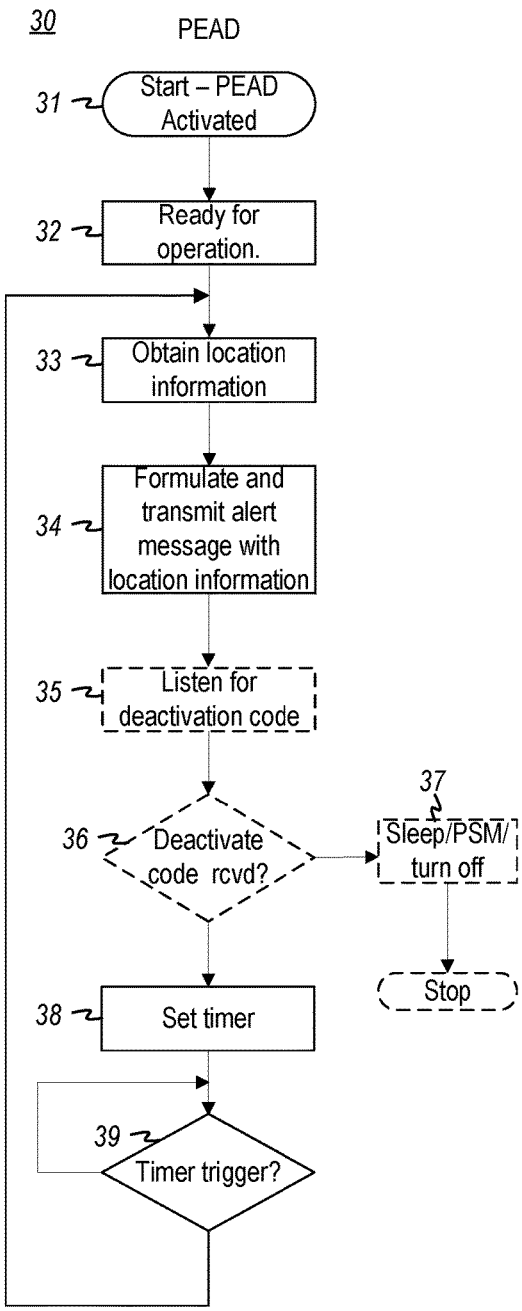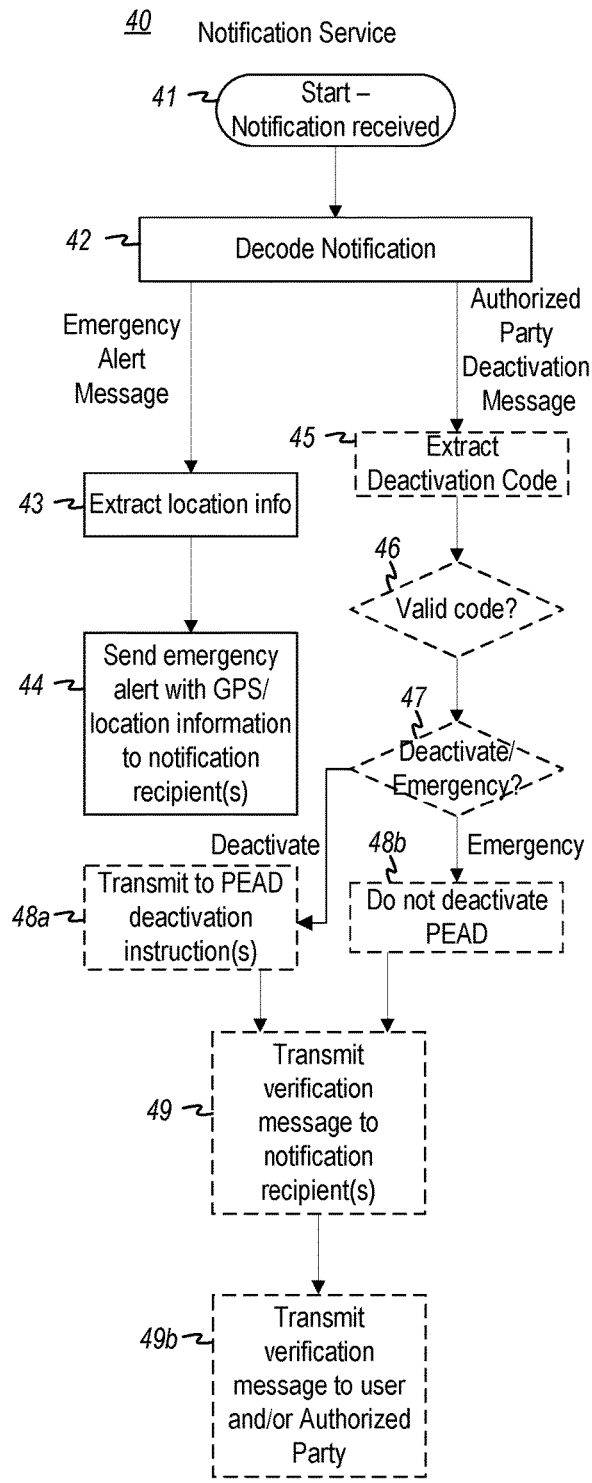
FIG. 3A
FIG. 3B

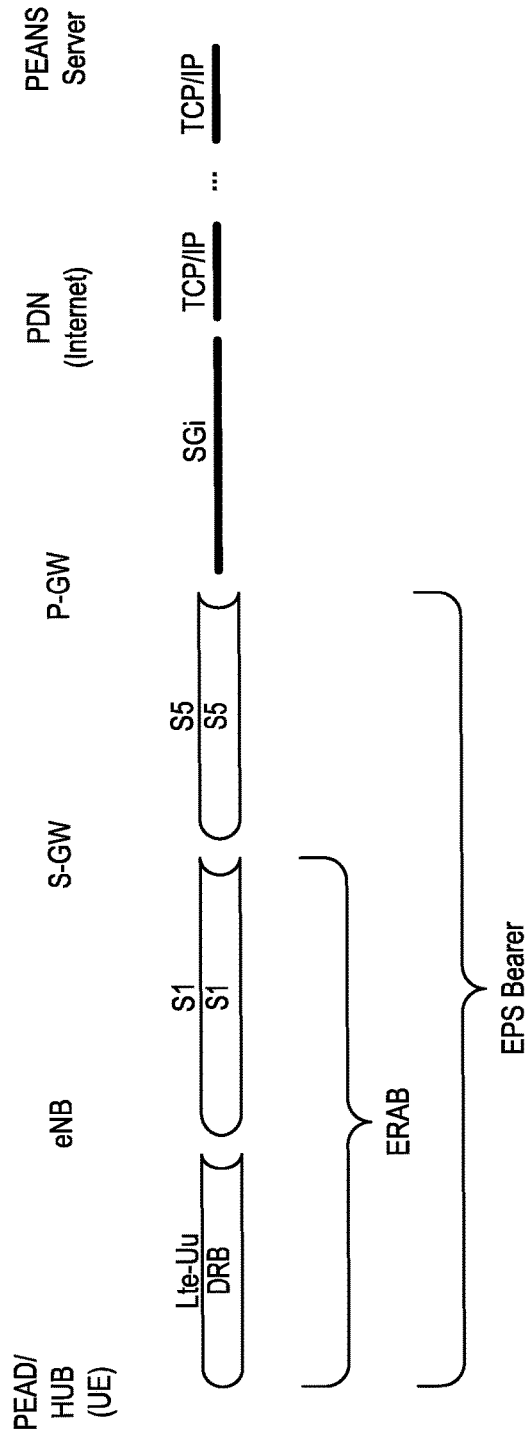
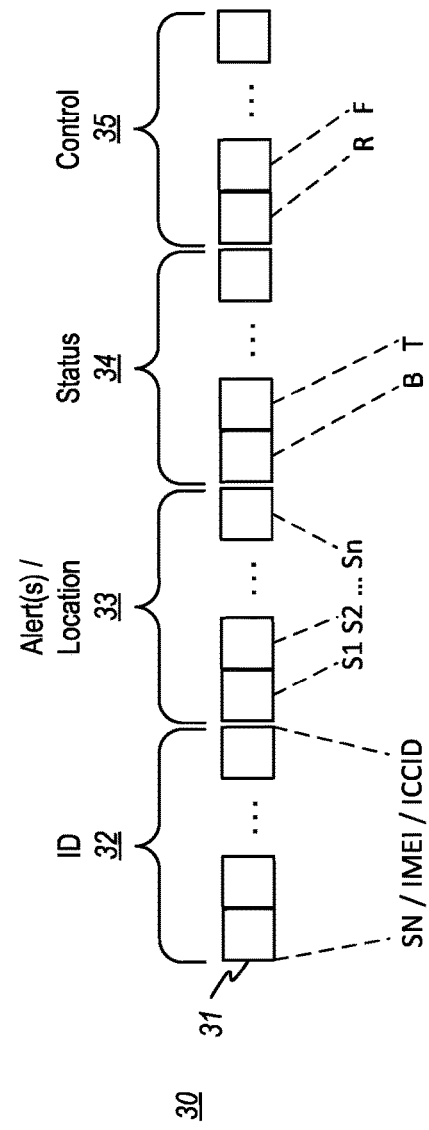
FIG. 5
FIG. 6A

PERSONAL EMERGENCY ALERT SYSTEM, METHOD AND DEVICE

BACKGROUND OF THE INVENTION

People often require help from other people in emergency situations. People living on their own may be fine most of the time, but an accident or condition (unexpected or otherwise) may render them in need of help. People can and do encounter unknown and/or risky situations, which can result in a person finding themselves in a dangerous or precarious situation from which they need extracting by, or assistance from, other people.

For example, elderly people with health conditions who live on their own may need to be able to seek immediate assistance from a remote person when they experience a health-related incident, accidentally fall or get injured. One popular solution to this problem is the emergence of personal emergency alert systems. Existing emergency alert systems generally consist of a wearable or wall-mounted emergency alert device that includes a simple user interface such as a button or voice-activated switch that automatically calls an emergency monitoring service upon activation via the user interface. The emergency monitoring service typically provides two-way communication between the person activating the emergency alert device and a human operator that can speak to the person to assess what emergency services, if any, need to be dispatched to the person. For example, if a person is having a health-related problem, the operator may connect the person to a health provider or dispatch an ambulance to the person's location. Such devices may be connected via a cellular connection, via WiFi using voice-over-IP, or via a landline. Because such devices need to be active all the time, and allow for 2-way communication, they also to be connected to a power outlet or require frequent battery recharging and/or replacement.

As another example, with the rise in popularity of Internet-based matchmaking and dating apps, people often venture out alone with other people who they may not know. On the occasion that such a person finds his or herself in a situation that feels or is unsafe, that person may want to be able to alert another person to come extract them from the situation or otherwise provide help. While most people are now armed with mobile phones, the unsafe situation that a person may be in may prevent that person from calling or texting someone using their mobile phone. For example, the person may not be in a location with adequate cellular coverage, or the mobile phone battery may be out of charge. As further example, in the situation of an abductor or assailant, the person's mobile phone may be removed from its owner's access.

Accordingly, existing personal emergency alert systems often fail just when they are most needed.

BRIEF SUMMARY OF THE INVENTION

The problems inherent in prior art personal emergency systems are solved by the novel system, method and device for monitoring and notifying emergency contacts of a personal emergency described herein. Such system includes a personal emergency alert device that is kept in accessible proximity to a user, and a personal emergency alert notification service available via a communications network. The personal emergency alert device monitors and detects the occurrence of an emergency activation event proximal to the user. When the personal emergency alert device detects an occurrence of such emergency activation event, it transmits an emergency alert message via the communications network to the remote personal emergency alert notification service. Upon receipt of the emergency alert message from the personal emergency alert device, the personal emergency alert notification service generates an emergency alert message and transmits an emergency alert event notification message to pre-designated emergency notification recipient(s). The personal emergency alert device periodically obtains the device geolocation and transmits the geolocation to the personal emergency alert notification service to allow the geolocation of the device (and presumably the user) to be tracked following the activation event.

In an embodiment, the system includes a personal emergency alert device comprising a cellular modem, a geolocation module arranged to obtain geolocation information representative of a geolocation of the device (for example, a GPS receiver), a sensor arranged to detect an activation event and to generate an activation signal upon detection of the activation event, a controller in electrical communication with the sensor, the cellular modem, and the geolocation module, and a power switch that switchably connects a power source to the controller, the sensor, the cellular modem, and the geolocation module to place the device into a power-on state. In operation, when the personal emergency alert device is placed into the power-on state, the controller instructs the cellular modem to establish radio access network bearers to create a data tunnel between the device and a packet data network through which the device can communicate with a personal emergency alert notification service accessible via the packet data network. The personal emergency alert device then goes into a low power mode until activated by an activation signal generated by the sensor upon occurrence of the activation event. Once activated, the controller repeatedly performs an operation of (a) instructing the geolocation module to obtain device geolocation information, (b) formulating an alert message comprising the obtained geolocation information, and (c) instructing the cellular modem to transmit the alert message to the personal emergency alert notification service via the data tunnel, the controller halting the repeated performance of the operation only when the device runs out of power. Alternatively, the device can be deactivated by an independent source other than the user or device itself, such as one of the designated notification recipients, contacting the personal emergency alert notification service, sending a valid deactivation code to the service, whereby the personal emergency alert notification service may then instruct the device to deactivate itself.

BRIEF DESCRIPTION OF THE DRAWINGS

A more complete appreciation of this invention, and many of the advantages thereof, will be readily apparent as the same becomes better understood by reference to the following detailed description when considered in conjunction with the accompanying drawings in which like reference symbols indicate the same or similar components, wherein:

FIG. 3A is a flowchart illustrating exemplary operational steps performed by an embodiment of a personal emergency alert device;

FIG. 3B is a flowchart illustrating exemplary operational steps performed by an embodiment of a personal emergency alert notification service;

FIG. 5 is a data flow diagram illustrating the network data gateways and protocols for transport of data between a personal emergency alert device and a personal emergency alert notification service;

FIG. 6A is a data format diagram illustrating an exemplary data format for an emergency alert message generated by a personal emergency alert device;

DETAILED DESCRIPTION OF THE INVENTION

Figure 1:
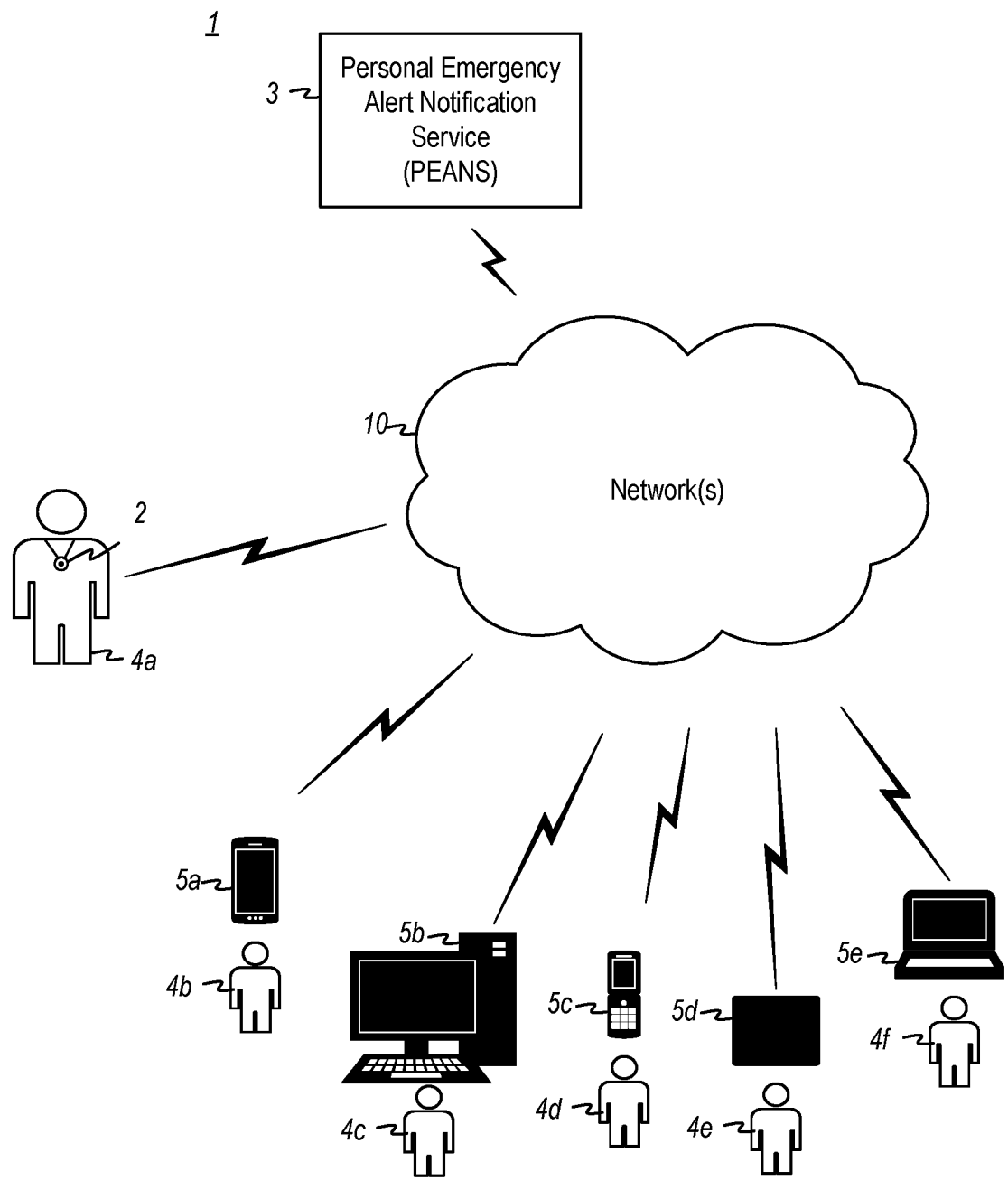
FIG. 1 is a system diagram of an exemplary environment implementing a personal emergency alert system in accordance with an embodiment of the invention.

Various embodiments are described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Referring now to FIG. 1, a personal emergency alert system 1 includes a personal emergency alert device (PEAD) 2 located in accessible proximity to a user 4*a*, a communications network 10, a personal emergency alert notification service (PEANS) 3 and one or more remote electronic user devices 5 (shown as 5*a*, 5*b*, 5*c*, 5*d*, 5*e*) accessible by corresponding people 4 and/or other electronic devices. PEAD 2 is maintained in proximity to user 4*a*. User 4*a* may carry, wear, or stay in accessible reach of, PEAD 2. If and when user 4*a* requires emergency help, the user 4*a* activates the PEAD 2. When activated, the PEAD 2 automatically powers up or wakes up from a power saving mode (PSM), enables geolocation functionality, and automatically connects to PEANS 3 and sends it an emergency alert. PEANS 3 then sends an emergency alert notification message to one or more $3^{rd}$-party notification recipients 4*b*, 4*c*, 4*d*, 4*e*, 4*f* (collectively, 4) indicating that user 4*a* requires emergency service. PEANS 3 alerts notification recipients via one or more of an SMS text message, an email, a phone call, an in-app alert, etc. In an embodiment, once the PEAD 2 is activated by the user 4*a*, it cannot be deactivated unless the PEANS 3 is contacted with a valid deactivation code by a source independent from PEAD 2. In an alternative embodiment, the PEAD 2 is a one-use device, and once activated, cannot be deactivated and will continue to report its location until it runs out of battery life.

Communications network(s) 10 may be any network or combination of networks that enables the transmission of an alert from PEAD 2 to PEANS 3, and further that enables PEANS 3 to transmit a notification message to the electronic device(s) 5*a*, 5*b*, 5*c*, 5*d*, 5*e* of the designated notification recipient(s) 4*b*, 4*c*, 4*d*, 4*e* associated with the PEAD 2. In various embodiments, the communications network 10 may comprise one or more, or a combination of, wireless and/or wired networks, such as but not limited to Wide Area Networks (WANs), Local Area Networks (LANs), Wireless LANs (WLANs), Low Power WANs (LPWANs), 3G, 4G and 5G cellular networks, Wi-Fi networks, satellite networks, wireless mesh networks (for example using a Zigbee standard protocol), Bluetooth, unlicensed RF network (e.g., 433 MHz unlicensed spectrum), etc.), and may thereby require use of, and (if required) translation between, various transport protocols, including by way of example and not limitation, TCP, TCP/IP, IP, Ethernet, Zigbee, Bluetooth, etc. In a preferred embodiment, the network(s) 10 is implemented, at least in part, as a LPWAN such as a 3GPP Long Term Evolution (LTE) CAT-M1 (or other enhanced Machine-Type Communication (eMTC) protocol, a Narrow-Band Internet of Things (NB-loT) protocol, or an Extended coverage GSM IoT (EC-GSM-IoT) protocol, as the communication link between PEAD 2 and PEANS 3.

Figure 2:
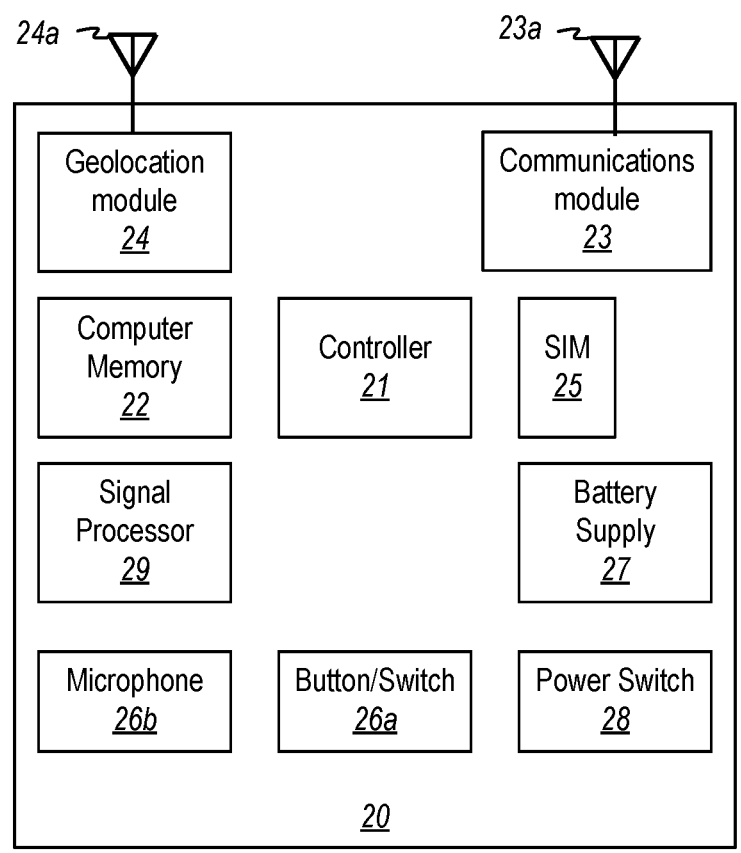
FIG. 2 is a block diagram illustrating an example embodiment of a personal emergency alert device implemented in accordance with the invention.

FIG. 2 depicts a block diagram of an example embodiment 20 of personal emergency alert device (PEAD) 2. In this embodiment, PEAD 20 includes a controller 21, computer memory 22, a communications module 23 with corresponding antenna 23*a*, a geolocation module 24 with corresponding antenna 24a, a Subscriber Identity Module (SIM) 25, one or more activation condition sensor(s) 26a, 26b, and corresponding sensor signal processing circuitry 29, and a battery supply 27 with optional power switch 28.

Controller 21 may be a microprocessor, a computer processing unit (CPU), a microcontroller unit (MCU), or custom application specific integrated circuit (ASIC), or other integrated circuit (IC), or non-integrated circuitry. Controller 21 is electrically coupled to (directly or indirectly), or has embedded therein, computer memory 22. Controller 21 may include several integrated devices; alternatively, peripheral devices can be connected to controller 21. For example, the controller 21 may have one or more internal timers or clocks (not shown) integrated into the controller 21 itself. Alternatively, PEAD 2 may include one or more timer ICs connected to the controller 21 via external pins. The timer(s) may be used in some embodiments to send wakeup commands to controller 21 to wake it up from PSM. The timer can be connected to an interrupt input of the controller 21. Upon expiration of the timer, the controller is interrupted and executes an interrupt service routine that causes the controller to exit PSM to perform periodic diagnostics or perform other functions. In an embodiment, the PEAD 20 may be wakened from PSM if PEAD 2 detects an activation event or if a predefined amount of time passes between times connecting to the subscriber network 10. This activity is called the "heartbeat" of the PEAD 2.

Computer memory 22 comprises computer readable storage media, preferably in the form of one or more, or any combination, of Programmable Read-Only Memory (PROM, EPROM, EEPROM, flash EPROM), and/or Random Access Memory (RAM, DRAM, SRAM, SDRAM, etc.). Memory 22 stores program instructions executable by the controller 21 to perform one or more operative steps for implementing various aspects of the invention. The computer memory 22 further stores data which may be used by the controller 21 in its operations. The computer memory 22 may be integrated or embedded within the integrated circuit (IC) implementing the controller 21 or may be standalone memory IC(s) electrically coupled to the controller 21 via one or more busses.

The computer memory 22 stores program instructions and data. Memory 22 may store a unique device serial number (SN). Battery supply 27 is electrically coupled to, and supplies power to, all the electronic components of the PEAD 20. Battery supply 27 may be controlled by a power switch 28.

Communications module 23 is electronic circuitry typically fabricated in the form of an integrated circuit (IC) that contains the hardware and control functions for implementing the RF communication. In particular, a typical communications module 23 contains a controller/CPU, integrated computer memory, signal encoding/decoding circuitry, a power amplifier, and a baseband processor which includes multiplexing/demultiplexing, channel selection, carrier generation, and modulation circuitry. In an embodiment, the communications module 23 is a cellular modem responsive to telephone Attention (AT) commands for controlling the modem, and converts digital messages into RF transmission signal suitable for the network on which it is transmitted. In an embodiment, where the communications module 23 is implemented to connect to an LTE or LTE-M cellular network, the communications module 23 is a cellular modem configured to transmit signals on the antenna 23a according to 3G, 4G, 5G, or CAT-M1 or NB-IoT protocol. Where the cellular modem is implemented to connect to a GSM network, it is configured to transmit signals on the antenna 23a according to a GSM or EC-GSM-IoT protocol. Communications module 23 may further be configured to receive RF signals carrying messages from PEANS 3 via network 10 (FIG. 1) and to convert the received signals into a digital format recognizable by the controller 21. Communications module 23 may include internal computer-readable memory which includes storage of an International Mobile Equipment Identifier (IMEI). SIM 25 stores a unique Integrated Circuit Card Identifier (ICCID) that is required to authenticate a subscriber of a cellular network service to such network and allow such subscriber access to the cellular network and corresponding service.

Communications module 23 adheres to a predetermined transmission protocol stack based on the protocol used for communicating with the cellular service to which the PEAD 2 subscribes. As is required generally for cellular modems that need to deliver messages from a mobile device through a cellular network to a packet data network (e.g. the Internet), communications module 23 includes circuitry and programming to encode an emergency alert message generated by the controller 21, encapsulate the encoded message into one or more packets, and perform the signal processing required to adhere to the data transmission scheme(s) recognized and used by the cellular network 110 for data uplink (from PEAD 2 to cellular network) and data downlink (from cellular network to PEAD 2). For example, where network 10 comprises an LTE-M enabled cellular network, the cellular modem preferably is capable of packetizing data in accordance with TCP/IP or UDP protocol, and includes hardware that transmits packet data according to a SC-FDMA, 15 KHz tone spacing, Turbo Code, 16 QAM modulation scheme, and receives data based on OFDMA, 15 KHz tone spacing, Turbo Code, 16 QAM modulation scheme. Other types of cellular networks use different modulation schemes implemented in accordance with the standards promulgated by worldwide organizations such as 3GPP, IEEE, and GSMA. Such alternative networks may alternatively be used as the gateway connection to a packet-switched data network (such as the Internet) for subsequent transmission of alert messages to PEANS 123.

Activation condition sensor(s) 26 (shown as 26a, 26b) comprise one or more sensors 26a, 26b that sense one or more alert activation conditions. For example, a manual activation sensor 26a may comprise a button or switch that a user can press or set to activate the personal emergency alert device 20 to generate an activation signal. In such embodiment, the manual activation 26a generates an output signal on at least one output port. The output port may be a pin, pad, wire, or connected trace on a PCB board. The state of the output signal represents an activation status of the sensor 26a. In an embodiment, the manual activation sensor 26a is implemented with a push-button switch. The activation status corresponds to an activation state when the push-button switch set to a first position (e.g., pressed down), and corresponds to a non-activated state when the push-button switch set to a second position (e.g., not pressed down). In a non-limiting illustrative embodiment, the manual activation sensor 26a is implemented using push-button switch; however, it is to be understood that other types of electronic and/or electromechanical switches may also be used without departing from the scope of the invention.

In another example, a voice-activation sensor 26b comprises a microphone. Microphone 26b detects sound (including voice) and passes signal data representing such detected sound to signal processor 29. Signal processor 29 processes incoming signal data, converts it to voice/sound data signature(s) in a known format, and compares such data signature(s) to predefined trigger signature(s) (stored in memory 22). (Alternatively, the controller 21 can perform the comparison). For example, in an embodiment, the PEAD 20 may be configured to store data signatures of prerecorded trigger words (e.g., "help" or "activate", etc.) spoken by the user, converted to a digital signature, and stored as predefined trigger signature(s) in computer memory 22. Other examples of predefined trigger signatures that may be stored in computer memory 22 may include signatures generated from sound alarms (such as fire or smoke alarms) or any other digital signature that can be generated from signals picked by a microphone.

While FIG. 2 illustrates a microphone 26b used in conjunction with a signal processor 29, it is to be understood that trigger signatures are not limited to signals that can be generated only from signals picked up by a microphone. Trigger signatures may be generated from any signal waveform generated by any electronic component. Accordingly, trigger signatures may be used to detect a waveform from one or more of the sensor(s) 26. In an embodiment, a sensor may be an accelerometer which generates a relatively consistent signature in terms of force or acoustics when certain actions are taken (e.g., a door slams open or closed). In each case, the controller 21 and/or signal processor 29 may be programmed to process, and recognize an activation signature from, a signature from one or more sensor(s) 26 (including, without limitation, one or more of a switch, a microphone, an accelerometer, a passive infra-red (PIR) sensor, a smoke/fume/CO2 sensor, an optical sensor, an electromagnetic switch (such as a reed switch), a Hall capacitance sensor, a temperature sensor, a humidity sensor, a pressure sensor, a positioning sensor, etc. Controller 21 may further be programmed to distinguish between different activation events based on signature(s) generated from different sensors 26 and/or different signature types obtained therefrom. The controller 21 can be programmed to classify received signature types into corresponding alert types, which can then be communicated to PEANS 3.

The PEAD 20 may comprise any number of activation condition sensors 26. While sensors 26a, 26b are illustrated for purposes of example, the PEAD 20 may additionally or alternatively include any one or more of a temperature sensor, a humidity sensor, a water level sensor, a motion sensor, a PIR sensor, a smoke sensor, a gaseous fume sensor, a CO2 sensor, and so on. When an activation condition sensor 26 senses or is otherwise set to an activation state, the sensor 26 (and associated signal processing circuitry 29) signals the controller 21. The controller may perform further processing to determine whether to send an alert message to PEANS 3 via the communications module 23, or may bypass further processing and directly send an alert message to PEANS 3 via the communications module 23. In embodiments, activation sensor(s) 26 may comprise Micro-Electro-Mechanical Systems (MEMS) comprising microfabricated miniaturized electro-mechanical elements (on the order of micro, femto and nano-meters) that by design consume very low power.

The PEAD 20 further comprises a geolocation module 24. In an embodiment, the geolocation module comprises a GPS module that includes a GPS receiver that receives signals from a Global Positioning System. The GPS module further includes a processor that converts received GPS signals into digital GPS geolocation coordinates. A log of the GPS coordinates over time may be stored in computer memory 22. Generally, as discussed below, the geolocation module 24 is not enabled unless and until instructed by the controller 21 based on detection of an activation condition at one of the sensors 26. The GPS module 24 may be implemented as a separate integrated circuit ("chip"), or could be embedded within the cellular modem chip 23. For example, as discussed in further detail hereinafter, the Quectel BG96 Cat.M1/NB1 & EGPRS Module optionally includes a GPS receiver and GPS processing circuitry for receiving GPS data from the Global Positioning Satellite System (GPSS).

Structurally, controller 21 is electrically coupled to receive a signal from each sensor 26 and/or its corresponding processing circuitry (such as signal processor 29). In an embodiment, the controller 21 is a microprocessor or microcontroller capable of receiving interrupt signals and processing interrupt service routines. In such embodiment, the controller 21 is coupled, directly or indirectly, to receive and process one or more activation signal(s) generated by the sensor(s) 26 and executes hardware logic or program instructions based on the received sensor activation signal(s). For example, in the case where a sensor 26 is a manual activation sensor 26a, the sensor 26a generates on a sensor output port a signal representing an activation status of the sensor. In an embodiment, the controller 21 comprises a microprocessor that is capable of processing an interrupt received on an interrupt input port (e.g, a pin or pad of the microprocessor). The output port of sensor 26a is electrically coupled (directly or indirectly) to an interrupt input port of the controller 21, and the signal present on the output port of manual activation sensor 26a serves as an interrupt signal to controller 21. When the button is pressed (or switch set to the position corresponding to an activation state), sensor 26a generates the signal corresponding to the activation state, thereby triggering an interrupt at controller 21.

In a similar manner, the signal processor 29 may generate an activation signal on an output pin or port that is electrically coupled to an interrupt input of the controller 21. The signal processor activation signal may be generated upon detection of a signature match between a predefined trigger signature and a digital signature it generates from signals it receives from the microphone 26b. Thus, when a user 4a speaks or otherwise vocalizes an activation word (such as "help!"), such activation condition is received by the microphone 26a, and processed into a digital signature by signal processor 29. The signal processor 29 (or controller 21) compares the newly processed digital signature with pre-stored activation signatures. If signature of the spoken activation word matches a pre-stored activation signature, the signal processor 29 (or controller 21) generates an activation signal on an output port. The output port is electrically coupled to a controller interrupt port, triggering an interrupt at controller 21.

Controller 21 executes one or more service routine(s) corresponding to the interrupt(s). In an embodiment, the interrupt service routine(s) includes program instructions executable by the controller 21 to formulate an alert message and send commands to the communications module 23 to transmit the alert message indicating the activation condition present at the personal emergency alert device 2. The interrupt service routine also includes program instructions executable by the controller 21 to activate the geolocation module 24 and begin collecting geolocation information, such as GPS coordinates, and periodically transmit the collected geolocation information to the emergency alert notification service 3. The controller 21 may send the GPS coordinate data along with each alert message. In an alternative embodiment, the controller 21 may be programmed to track the GPS coordinate data, determine whether the PEAD 20 has moved from a previous location, and then track the GPS coordinate data, and transmit the GPS coordinate data on a programmed time basis.

FIGS. 3A and 3B illustrate the operation of PEAD 2 and PEANS 3. As previously mentioned, the user 4a maintains the PEAD 2 in accessible proximity. The user 4a activates the PEAD 2 directly using the activation mechanism. In an embodiment, the activation mechanism may be a button or switch, a microphone, or other activation sensor that can be activated via user interaction. In alternative embodiments, the activation mechanism may include sensors that monitor environmental conditions, such as a smoke, gas, and/or CO2 detector, a sound alarm detector, a PIR sensor, a temperature and/or humidity sensor, etc. and activate upon detection of a condition above and/or below corresponding respective threshold(s).

FIG. 3A depicts the operation of the PEAD 2. The PEAD 2 is activated (step 31). In an embodiment, the PEAD is activated directly by the user 4a. In an alternative environment, the PEAD 2 is activated indirectly by environment-monitoring sensor(s). Upon activation, the PEAD 2 readies itself for operation (step 32). In an embodiment, the PEAD 2 is not connected to power until manually activated by the user 4a, for example by pushing a button on the PEAD 2. Accordingly, the activation sensor could be the power on button that turns on power to the device. In an alternative embodiment, prior to first use, the PEAD 2 is powered on and initialized and then placed in a low power, sleep, or power saving mode. Then, upon manual or sensor-enabled activation, the PEAD 2 readies itself by powering up, or waking up from low power, sleep or power saving mode (PSM), and turning on and otherwise readying the various PEAD components. When waking from in a low power mode, sleep or PSM, the PEAD 2 may be activated through user interaction with a button, a switch, a microphone (speaking a predefined activation word) or other sensor capable of user interaction, or alternatively may be activated through sensor detection of predefined environmental conditions. Readying the PEAD 2 for operation may include, in addition to powering on, without limitation, any one or more of: waking up or coming out of PSM, enabling the communications and geolocation modules 23, 24, turning on antennas 23a, 24a, setting up a connection to the PEANS 3, and instructing the geolocation module 24 to begin collecting location information (such as GPS coordinates).

Once readied for operation, the PEAD 2 retrieves first location information (such as current GPS coordinates) (step 33) and formulates and transmits an alert message including location information to the PEANS 3 (step 34). In an embodiment, the PEAD 2 then sets a timer to a predefined time interval (step 38), and waits for the timer to expire (step 39). When the timer expires, the PEAD 2 repeats steps 33-39, collecting and transmitting PEAD location information at timed intervals. In an embodiment, the PEAD 2 is designed to disallow turning off the alert/location transmissions to the PEANS 3 once the PEAD 2 is activated. This ensures that the location of the PEAD 2 (and location of a user 4a having the PEAD 2 on their person) will continue to be sent to the PEANS 3 until the battery supply 27 can no longer supply sufficient energy to support the PEAD 2. This prevents turning off of the PEAD 2 by the user 4a (or another person having physical access to the PEAD 2) in situations where the user 4a is under duress (such as when someone else is forcing user 4a to deactivate the PEAD 2).

In an alternative embodiment, once PEAD 2 is activated, the PEAD 2 can only be deactivated by an independent source (not the PEAD 2) sending a predefined deactivation code to PEANS 3. In this case, PEAD 2 listens for a deactivation code (step 35), and if a deactivation code is received (step 36), PEAD 2 automatically deactivates itself by powering down, or putting itself in sleep mode or PSM (step 37).

With reference to FIG. 3B, PEANS 3 receives notifications (step 41) from the PEAD 2 and from notification recipients and/or other $3^{rd}$-party sources (for example, emergency services entities such as police or EMT organizations). The PEAD 2 decodes each notification 42. If the notification is from the PEAD 2 (i.e., an emergency alert message), PEANS 3 extracts the location information from the message (and any additional information available included in the alert message from the PEAD 2) (step 42) and sends an emergency alert message containing location information to one or more electronic device(s) of one or more corresponding designated notification recipients (step 44). Notification recipients may be individuals such as family, friends and caregivers, and/or emergency service providers such as 911-monitoring services, police, fire and/or EMT organizations, corporate or governmental agencies or service providers. Notification recipients may also be electronic systems and/or equipment that can provide or summon emergency services.

Notification recipients can take action based on the information received in the emergency alert message. For example, notification recipients may be, or can call, emergency service providers (e.g., 911 services, police, fire, EMT and/or other services, etc.). Notification recipients may also attempt to call the user 4a in the hope that the user 4a has a mobile phone capable of receiving a call. (Of course, such action may not be prudent if the user is under duress and used the PEAD 2 to inform others that the user 2 is in trouble but cannot risk using their mobile phone).

Notification recipients can track the location of the user 4a (or technically the location of the PEAD 2), through periodic timed notification messages transmitted by the PEAD 2, and may themselves, or may direct someone else, to physically go to the location indicated by the PEAD 2 in order to provide assistance to the user 4a.

Deactivation

Occasionally a PEAD 2 may be activated accidentally or the emergency situation is resolved and the user 4a no longer needs physical help. In such situations, it may be desirable to allow deactivation of the PEAD 2. In an embodiment, the transmissions by the PEAD 2 may be deactivated by an independent party. In an embodiment, PEANS 3 must receive a valid deactivation code from an independent source (i.e., not the PEAD 2, and preferably not the user 4a). Preferably, the deactivation code is known only by the notification recipients and/or other $3^{rd}$ party agencies (such as emergency services) ("authorized parties"). The authorized parties may or may not include user 4a. As an additional line of security, "authorized parties" would not include user 4a. Authorized parties can send the deactivation code to PEANS 3 to deactivate the PEAD 2. The deactivation code is preferably used only when the individual or entity deactivating the PEAD 2 knows or is informed that the user 4a is safe (preferably through personal knowledge or a trusted source). In an embodiment, PEANS 3 provides one or more application programming interfaces (APIs) through which it receives messages from authorized parties. For example, PEANS 3 may provide an API for receiving SMS text messages containing a deactivation code. As further example, PEANS 3 may provide an API for receiving email messages containing a deactivation code. In yet a further example, PEANS 3 may provide an API for receiving a deactivation code from an authorized party via an app executing on the authorized party's electronic device (e.g., a mobile phone, tablet, computer).

Returning to FIG. 3B, when an authorized party notification message is sent to PEANS 3, PEANS 3 receives (step 41) and decodes (step 42) the notification message, extracts the deactivation code from the message (step 45) and determines whether the deactivation code is valid (step 46). If the deactivation code is invalid, PEANS 3 will not deactivate the PEAD 2 and the message is either ignored or PEANS 3 sends a message back to the message sender indicating that the code is invalid.

Upon determination of a valid deactivation code (step 46), PEANS 3 may take further action. In an embodiment, given a valid deactivation code PEANS 3 simply sends a deactivation instruction to the PEAD 2 (step 48*a*). In an embodiment, as described in detail hereinafter, the notification service 40 can only communicate with the PEAD 2 if and when the PEAD 2 connects to the notification service 40. Accordingly, in such embodiment, PEANS 3 sends deactivation instructions to the PEAD 2 on the next connection by the PEAD 2 to PEANS 3. In an alternative embodiment, once activated (step 31) and readied for operation (step 32), the PEAD 2 remains connected to PEANS 3 until it either receives deactivation instructions from PEANS 3 or runs out of battery life. In such embodiment, PEANS 3 can transmit deactivation instructions to the PEAD 2 on demand since, once activated, the PEAD 2 is always connected to PEANS 3.

In an alternative embodiment, PEANS 3 provides a secondary emergency notification feature that allows the user 4*a* to notify PEANS 3 that the emergency notification message sent by the PEAD 2 is a true emergency request (in the guise of a deactivation request) or a true deactivation request. To this end, the user 4*a* may send an authorized party deactivation message to PEANS 3 via an independent electronic device other than the PEAD 2. In this embodiment, the deactivation code may indicate that the message is either a true deactivation request or a true emergency request. The code corresponding to a true emergency request is preferably known only by the user 4*a* (and optionally to other authorized users) and is stored with or is accessible by PEANS 3. Preferably, the user interface through which user 4*a* enters the code equating to the true emergency request (the "true emergency code") is identical to the user interface through which the user 4*a* enters the code equating to a true deactivation request (the "true deactivation code"). In this way, the user 4*a* can enter a true emergency code under the guise of entering a deactivation code in the situation where the user 4*a* is under duress (e.g., an assailant is watching the user 4*a* enter the code). In implementation, PEANS 3 validates the deactivation code (step 46) and determines whether the validated deactivation code is a true deactivation code or to an true emergency code (step 47). If the deactivation code is a true deactivation code, PEANS 3 transmits deactivation instruction(s) to the PEAD 2 (step 48*a*) and optionally transmits a deactivation verification message to the authorized party (either to all authorized parties or only to the particular authorized party who sent the deactivation message to PEANS 3) (step 49). If, on the other hand, the deactivation code is a true emergency code, PEANS 3 does not transmit deactivation instruction(s) to the PEAD 2 (step 48*b*) and optionally transmits a verified emergency message to the notification recipients (preferably not including the user 4*a*) (step 49). PEANS 3 also optionally sends a dummy (i.e., a "fake") deactivation verification message to the user 4*a* or authorized party who initiated the authorized party deactivation message (step 49*b*) to make it appear that the PEAD 2 has been deactivated, when in fact the PEAD 2 has not been deactivated.

In preferred embodiments, PEAD 2 is (1) portable and (2) operates even in remote locations that may not have access to power and/or (reliable) WiFi for accessing the Internet 120. To this end, (1) power to PEAD 2 is supplied from a battery supply (or optionally a standalone power source such as a solar power supply) (allowing for portability), (2) PEAD 2 is implemented using low power components and power saving methodologies (maximizing battery life), and (3) PEAD 2 accesses the Internet 120 to communicate with personal emergency alert notification service 123 using a Low Power Wide Area Network (LPWAN) to support long-lasting battery life (also maximizing battery life). The result is a long-lasting low-power personal emergency alert system that allows a PEAD 2 to be worn, carried on one's person, and/or installed in accessible proximity to a user 4*a* in a multitude of different environments, including in remote locations and deep within buildings.

Figure 4:
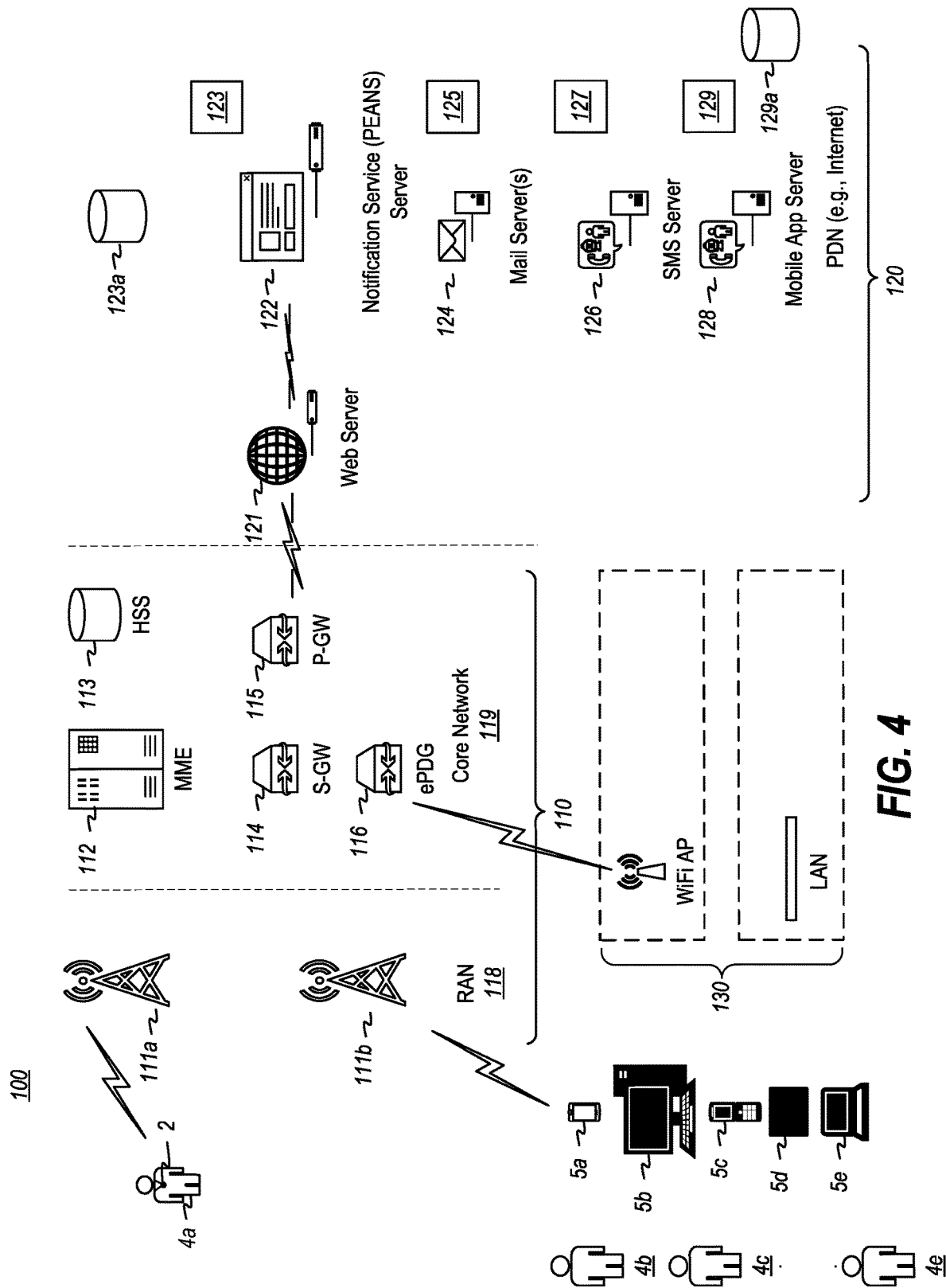
FIG. 4 is a system diagram illustrating an exemplary networked environment for operating a personal emergency alert system.

FIG. 4 shows an exemplary embodiment of a network environment 100 implementing a personal emergency alert system 100 and further implemented according to the above-mentioned power conservation objectives. PEAD 2 may be implemented according to the embodiment 20 in FIG. 2. Prior to use, PEAD 2 is registered with a personal emergency alert notification service 3 (shown as 123 in FIG. 4). In a preferred embodiment the personal emergency alert notification service (PEAMS) 123 is accessible via a packet data network (PDN) such as the Internet, but it is to be understood that an emergency alert message may be transmitted from the PEAD 2 and routed to the notification service 123 across multiple different networks having different physical and logical communication transmission stacks/protocols, such as one or more different cellular networks and/or one or more different packet data networks.

PEANS 123 stores registration information in a database 123*a*. The registration information stored in database 123*a* includes the PEAD identifier, along with corresponding notification recipient and corresponding delivery service information. In an embodiment, database 123*a* stores the device ID of each registered PEAD 2, along with, for each device ID, one or more electronic device delivery addresses of notification recipients and corresponding indications of electronic delivery services which are to be used to deliver a notification to the corresponding respective delivery addresses. Such schema allows one or more notification recipients to be notified via various notification delivery mechanisms. For example, for a given registered PEAD 2, a notification message may be sent to one or more recipients via their respective chosen notification delivery service (e.g., email, SMS text, in-app push notification, etc.) so that they can receive notification via their respective preferred technology.

For example, for a given registered PEAD 2, the device may be configured such that a notification is delivered via email to a particular notification recipient's email address, via SMS text to a recipient's mobile phone number, and to a recipient's app executing on the recipient's smart phone (addressed via the smart phone number or email address). A different registered PEAD 2 (not shown) having a different device ID may be configured such that a notification is delivered, for example, only via SMS text to a different recipient's mobile phone number. The described registration schema contemplates the ability to allow different registered devices to be individually configured such that notification recipient information and preferences can be specified on a device-by-device basis—that is, on a per PEAD basis. In embodiments, users of the personal emergency alert notification service 123 can select the notification delivery service(s) and corresponding notification recipients to be notified by the service, via a web-enabled app, a website portal or API. While it is contemplated that the notification service 123 supports user-configurable notification preferences, it is also within the scope of the invention that the notification delivery service(s) and notification recipients are predetermined by an administrator, and enterprise-level entity or other entity.

In operation, PEAD 2 may be activated per previous discussion. In system 100, PEAD 2 connects through a Low-Power Cellular Network 110 (shown as an LTE-M network) to the Internet 120, to send an emergency alert message to PEANS 123. PEANS 123 is connected to the Internet 123 by way of an Internet-enabled PEANS server 122. PEANS server 122 passes received emergency alert messages originating from PEAD 2 to PEANS 123. PEANS 123 parses and decodes each received emergency alert message, validates the message, and for valid messages, generates and sends an emergency notification message to designated notification recipient(s) associated with the PEAD 2. PEANS 123 may send such emergency alert message via pre-designated notification delivery services 125, 127, 129 associated with each respective notification recipient(s). In an embodiment, the notification service(s) comprise Internet-enabled services, such as an email service 125, an SMS text service 127, and an app push notification service 129. Such services connect to the Internet via servers 124, 126, 128, respectively, which route the emergency notification message(s) to one or more electronic device(s) 5a, 5b, 5c, 5d, 5e of designated notification recipients 4b, 4c, 4d, 4e. The messages may be routed through the Internet to another network, such as a cellular network, a WiFi network, a LAN, etc. to reach the intended destination (i.e., an electronic device 5 capable of receiving the notification message(s) via the corresponding delivery service(s).

In system 100 PEAD 2 AND Notification Service 123 communicate via a combination of networks, including a cellular network 110 and Packet Data Network 120 (such as the Internet). Preferably, the cellular network 110 is a Low Power Wide Area Network (LPWAN) that supports low-complexity, deep-coverage devices. Without limitation, exemplary LPWANs include LTE-M (including CAT-M1), NB-IOT and EC-GSM-IOT cellular networks.

LTE-M (also known as LTE CAT-M1) is a Third Generation Partnership Project (3GPP) standards-based LPWAN technology, having a maximum channel bandwidth of 1.4 MHz, a maximum data rate of 1 Mbit/s, and operates in either full or half duplex mode (i.e., can transmit and receive simultaneously in full duplex mode, or can only transmit or receive at any given time in half duplex mode). NB-loT (also known as CAT-NB1 or CAT-M2) is also a 3GPP standards-based LPWAN technology, having a maximum channel bandwidth of 180 kHz, a maximum data rate of 250 Kbit/s, and operates only in a half duplex mode. In another alternative implementation, the cellular network could be implemented according to the EC-GSM (or Extended Coverage Global System for Mobile, also called EC-GSM-IOT) is a Global System for Mobile Communications Association (GSMA) standards-based LPWAN technology which also operates in the licensed spectrum (on the 900 MHz and 1.8 GHz frequency bands) and implements EC-GSM protocols utilizing the existing GSM networks and GSM cellular to Internet infrastructure. Table 1 summarizes some of the main specifications for each of the LTE CAT-M1, CAT-NB1 and EC-GSM-IoT standards.

TABLE 1

| | CAT-M1 | NBIoT | EC-GSM-IoT |
|---|---|---|---|
| Deployment | LTE | LTE | GSM |
| Coverage | 155.7 dB | 164 dB | 164 db, with 33 dBm power class, 154 dB with 23 dBm power class |
| Downlink | OFDMA, 15 KHz tone spacing Turbo Code 16 QAM 1Rx | OFDMA 15 KHz tone spacing 1Rx | TDMA/FDMA, GMSK and 8PSK, 1Rx |
| Uplink | SC-FDMA 15 KHz tone spacing Turbo code, 16 QAM | SCFDMA 15 KHz tone spacing Turbo code | TDMA/FDMA, GMSK and 8PSK (optional) |
| Bandwidth | 1.08 MHz | 180 KHz | 200 kHz per channel, typical system bandwidth of 2.4 MHz |
| Peak rate (DL/UL) | DL and UL: 1 Mbps | DL: 50 kbps UL: 50 Kbps for multi-tone, 20 Kpbs for single tone | DL and UL: 70 kbps (GMSK) using 4 timeslots |
| Duplexing | FD & HD (type B), FDD & TDD | HD (type B), FDD | HD, FDD |
| Power saving | PSM, ext. I-DRX, C-DRX | PSM, ext I-DRX, C-DRX | PSM, ext. I-DRX |
| Power class | 23 dBm 20 dBm | 23 dBm | 33 dBm 23 dBm |

The particular type of cellular network that may be used for transmission of an alert message between a given PEAD 2 and the Notification service 123 may depend on various factors, including availability of a given type of cellular network in the geographical region where the PEAD module is installed, whether the PEAD module is authorized to access an available cellular network, how much data and how quickly such data needs to be transmitted to the PEANS, etc.

It is to be noted that commercial networks implemented in accordance with any of the LTE CAT-M1, CAT-NB1 and EC-GSM-IoT standards operate in the licensed spectrum of the radio-frequency spectrum (meaning that the frequency bands on which they operate are regulated by governmental regulatory bodies). Operation within the licensed spectrum requires operators to obtain a license or permit from a regulatory authority and to adhere to a set of technical, operational and behavioral rules, having the effect of potentially offering a higher quality of service (QOS) for delivery of communications between the PEAD 2 and the notification service 123 than may otherwise be obtained using networks operating in the unlicensed spectrum. It may therefore be advantageous to use such an available cellular network to communicate PEAD module alert messages from the PEAD 2 to the Notification service 123. However, it is to be understood that in other embodiments, it may be suitable or advantageous to use a LPWA network operating in an unlicensed frequency band of the radiofrequency spectrum. Examples of such networks may include, but are not limited to, LoRa, SigFox, etc. Furthermore, while a preferred embodiment of the PEAD module is battery powered and therefore to conserve power connects to the Notification Service via a LPWAN, in alternative embodiments where power consumption is not at issue for the PEAD module, the PEAD module may be implemented using a transmission module that allows it to transmit its alert messages via any wireless or wired network (including, but not limited to, LPWANs, LANs, WANs, WiFi Access Points, etc.) using an appropriate corresponding transmission protocol. For example, if the PEAD module is not positioned in a remote location and has access to a Wi-Fi Access Point, the PEAD module could be configured to include a WiFi transmission module and to send its alert messages to the Notification Service by connecting to the Internet via a local WiFi Access Point. Similarly, if WiFi is not available but a cellular service (that is not an LPWAN) is available, the PEAD 2 could include transmission module that can communicate with the available cellular service (which may not be an LPWAN) and could then transmit its alert messages via that cellular service.

In a preferred embodiment shown in FIG. 4, the LPWAN implements the 3GPP LTE-M (CAT-M1) specification and protocol, which support devices characterized by low power transmission (max transmit power of 23 dBm), provides a low maximum system bandwidth (1.4 MHz), and allows a relatively low maximum peak data rate (1 Mbps). In this embodiment, the PEAD 2 is configured to transmit alert messages over a radio access network (RAN) 118 that supports low power wide area network technologies. In the embodiment shown in FIG. 4, the radio access network 118 is a cellular LTE-M network operating in the licensed (i.e., regulated) spectrum. The LTE-M network operates over the same (or subset thereof) frequency bands as LTE) and implements 3GPP LTE-M specifications and protocols utilizing the existing LTE cellular infrastructure. The RAN 118 in the LTE cellular network includes what is referred to as the Evolved Universal Mobile Telecommunications System (E-UMTS) Terrestrial Radio. Access Network (E-UTRAN), and a core all-IP network 119 referred to as the Evolved Packet Core (EPC).

The E-UTRAN includes a network of cellular sites 111 (shown as 111a, 111b) providing areas of network coverage arranged in geographical "cells" across areas of Earth. Each cellular site includes at least one antenna mounted on a cell tower, which is designed to transmit and/or receive signals on a designated LTE-M frequency band. Within a given cell, transmitted signals adhere to minimum signal strength specifications so as to cover at least the entire area of the geographical cell. In practice, each cellular tower has multiple antennas sending and receiving over multiple LTE/LTE-M frequency bands, and each antenna is tuned to receive and/or transmit signals on various frequencies and in different directions. Each antenna is connected by wire or fiber optic cable to a base station (which in the LTE/LTE-M RAN is referred to as an Evolved Node B, eNodeB, or eNB).

The base station, or eNB, is the primary interface for connecting subscribing user equipment devices (UEs) to other devices and services serviced by the particular LTE/LTE-M network service provider (often called the "carrier", such as commercial providers Verizon, AT&T, etc.). The base station is also the primary interface for connecting subscribing devices via networks of other providers (such as routing calls to UEs who subscribe to a different carrier than the sending UE, and to devices, machines and services on other networks (such as other RANs, packet switched and packet data networks). The eNB manages the radio interface between user equipment (UE) devices (such as mobile and/or remote LTE and LTE-M enabled devices) and the core network (referred to as the Evolved Packet Core (EPC)) which connects and routes messages between remote UEs subscribing to the LTE/LTE-M cellular network and UEs and other devices on networks of other carriers or packet data networks such as the Internet.

Radio access network (RAN) 118 provides connection between LTE-enabled devices and the core network 119. The core network 119, or EPC, is an all-IP (Internet Protocol) network that manages the interconnection of calls and data flow between devices connected to the RAN 118, to one another and to other networks 130 and/or packet data networks (PDNs) 120 and resources connected to the core network 119. The core network 119 forms the central control of the cellular network 110. Among other functions, core network 119 manages authentication of user equipment (UE) (such as PEAD 2 and other UE such as cellular enabled mobile devices) requesting access to cellular network 110, voice/data call and message control/switching/routing, allocating resources to meet subscriber quality of service levels, and setting up data traffic tunnels (known as bearers) between authenticated UEs to packet data network (PDN) gateways 115 for transfer of user traffic between UEs and PDNs (such as the Internet 120).

In the LTE/LTE-M network, the core network (EPC) 119 includes a Mobility Management Entity (MME) 112, a Home Subscriber Server (HSS) 113, a Serving Gateway (S-GW) 114, a Packet Data Network Gateway (P-GW) 115. The MME 112 operates as the main control entity for the LTE radio access network (E-UTRAN) (which, in an LTE/LTE-M network, implements the RAN 118). The MME 112, with the assistance of a UE-connecting eNB 111, and a Home Subscriber Server (HSS) 113 that hosts network subscriber information, manages authentication of devices requesting access to the network 110. The MME 112 also manages control plane (Non-Access Stratum (NAS)) signaling, including mobility management, session management, and setup of tunnels, or "bearers" that carry user plane traffic. The MME 112 communicates with eNBs 111a, 111b, (and others not shown) in the radio access network 118 via the LTE S1-MME interface, while eNBs communicate with UEs via the LTE-Uu interface. When a UE requests access to the network, the eNB with greatest signal strength (usually the eNB nearest the requesting UE), along with both the UE and the MME serving the eNB, coordinate with each other to perform mutual authentication. In LTE networks, both LTE-enabled UEs and the LTE network follow well-known pre-defined LTE authentication protocols to ensure, from the UE's point of view, that the UE is accessing the network it thinks it is accessing and, from the network's point of view, that the UE has authorization to access the network and is who the UE says it is. The communication interfaces and protocols for LTE-M, including among others the LTE-UU, LTE-S1, LTE-S5 and SGi interfaces, are specified and published by $3^{rd}$ Generation Partnership Project (3GPP), available at www.3gpp.org.

When PEAD 2 is authenticated, the MME 112 sets up an IP connection (or "session") between the PEAD 2 and a particular Packet Data Network (PDN) through which PEANS 123 is accessible. Profile information associated with the authenticated PEAD 2 is accessible through the Home Subscriber Server 113 (and/or a Profile Repository (not shown)), which stores default PDN IP address associated with the PEAD 2. The PEAD 2 can also specify a specific IP address during the access request. The MME 112 determines the IP address of the PDN of the PEAD 2 requesting connection, using the default IP address from the PEAD 2 profile information or from PEAD 2 request information. The PEAD 2 can have either a static IP address or may be dynamically assigned an IP address using standard Dynamic Host Configuration Protocol (DHCP) or other dynamic IP address allocation protocols. The session identifies the connection endpoint IP addresses, namely the IP address of the PEAD 2 and the IP address of the PDN (also called the Access Point Name (APN)) through which the PEAD 2 wishes to connect (presumably to use services).

In conjunction with setting up the session, the MME 112 also sets up a default Evolved Packet System (EPS) bearer, which is a tunnel through which IP packets are transferred through the LTE network 110 between the PEAD 2 and a PDN gateway (P-GW) that serves the destination PDN. With reference to FIG. 5, the default EPS bearer requires setting up of three different bearers due to the different communication interfaces between equipment located between the PEAD 2 (UE) and P-GW (including the eNB, the S-GW and the P-GW). In the UE-to-P-GW direction, data flows from the UE to an eNB 111 via a data radio bearer (DRB) using the LTE-Uu interface, then from the eNB to the S-GW via the S1 interface, then from the serving gateway (S-GW) to the PDN Gateway (P-GW) using the LTE S5 interface. Accordingly three different bearers are set up to accommodate the different interfaces, which include a DRB (i.e., data tunnel) to deliver user data traffic between the UE and eNB using the LTE-Uu interface, an S1 bearer to deliver user data traffic between the eNB and S-GW, and an S5 bearer to deliver user data traffic between the S-GW and P-GW. The MME coordinates with the eNB, the S-GW and P-GW to set up these bearers.

FIG. 4 details a small few cellular sites (eNBs) 111a, ..., 111b, a single MME 112, S-GW 114 and P-GW 115, for the purposes of simplicity of illustration and explanation and not by way of limitation. It is to be understood that in practice, commercial LTE/LTE-M networks comprise many cellular sites 111, which may connect to several different MMEs, which are each connected to several S-GWs and P-GWs, serving different geographical locations of the overall cellular network. In an embodiment, the cellular network service provider through which PEAD modules gain access to the cellular network for subsequent transmission and receipt of messages over the Internet to and from the Notification Service is a $3^{rd}$-party commercial cellular network service provider that supports LTE-M, such as, by way of example only and not limitation, Verizon or AT&T.

LTE/LTE-M networks are all-IP networks, meaning that all user traffic is delivered by way of Internet Protocol (IP) packets. When an LTE-enabled UE, such as PEAD 2 connects to the network, it is assigned an IP address, a session is set up, and data traffic bearers are set up between the UE device and a PDN gateway P-GW. The IP address assigned to the PEAD 2 remains valid and the bearers remain connected until the device is detached from the network. That is, the session remains valid until the PEAD 2 is detached from the network. In the network system of FIG. 4, since the LTE-M network is an all-IP network, the PEAD 2 uses the IP protocol for sending alert messages to the notification system 123. In particular, the PEAD 2 encodes an alert message (called the message payload) and formulates it into at least one IP packet containing an IP header and the message payload.

FIG. 6A illustrates an example format of a message payload for purposes of illustration and not limitation. As illustrated, the message payload comprises one or more bytes 30 of bits 31. Groupings of the bits 31 correspond to encoded information. For example, one group 32 of bits 31 corresponds to encoded PEAD module identification (ID) information that uniquely identifies the PEAD 2 to PEANS 123. In an embodiment, the ID group 32 comprises the serial number (SN) or an encoded version of the serial number of PEAD 2. It may further include or alternatively include additional device information such as the International Mobile Equipment Identifier (IMEI) and/or the Integrated Circuit Card Identifier (ICCID) of the SIM card or hardware embedded in the PEAD 2.

Another group 33 of bits 31 corresponds to encoded alert information, which comprises a plurality of bits having values that may be encoded to represent one or more event(s) corresponding to one or more respective monitored event occurrences at PEAD 2. For example, alert information group 33 may include a bit S1 corresponding to a first sensor monitoring the occurrence of a first event, a second bit S2 corresponding to a second sensor monitoring the occurrence of a second event, and so on, monitoring up to n events. As a non-limiting example, the alert group 33 may comprise one or more individual bits corresponding to detected events including, without limitation: a push-button activation event, a voice-activation event, and a Low Battery event. The alert group 33 may comprise different and/or additional bits to represent various other detected events and/or change in states(s) of additional monitored activation conditions. In a more further detailed example, and with reference to FIG. 6A, bit 51 may represent the state of the occurrence of a push-button manual activation event, which when true (for example, set to a predefined value such as "1"), indicates that the button on the push-button 26a at PEAD 2 has been pushed. Further in the more detailed example, the bit S2 may represent the state of the occurrence of a voice-activation event detected via the microphone 26b at PEAD 2. Other bits may represent the occurrence of other events monitored by additional sensors. Furthermore, the Alert group 33 may include dedicated bits corresponding to location information related to the movement, such as but not limited to current GPS coordinates, most recent prior GPS coordinates, GPS coordinates of initial location of PEAD 2, etc.

In the message payload 30, another group 34 of bits 31 corresponds to encoded status information. For example, a bit B may represent the state of a battery low condition, while a bit T may represent an alert trigger state indicating whether or not an activation condition was detected by one or more sensors. Further in the message payload 30, a group 35 of bits 31 may correspond to encoded control information. In the illustrative embodiment, control bits may be used to hold the connection open between the PEAD module 300 and PEANS 123 in order to perform certain maintenance actions or actions that require 2-way cooperation with and/or acknowledgement between the PEAD module 300 and Notification Service 123. For example, again by way of illustration and not limitation, the Control group 34 may comprise a bit R which indicates to the Notification Service that the PEAD module 300 has been reset. The Control group 34 may further comprise a bit F indicating that the device has been formatted or updated with new firmware.

Figure 6B:
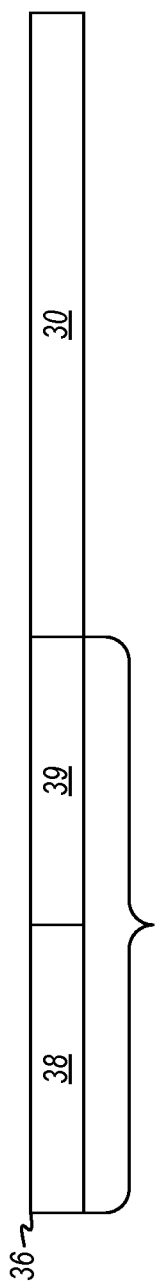
FIG. 6B is a data format diagram illustrating an exemplary IP packet format for transmitting a message payload from a personal emergency alert device to a nearby eNB.
Figure 6C:
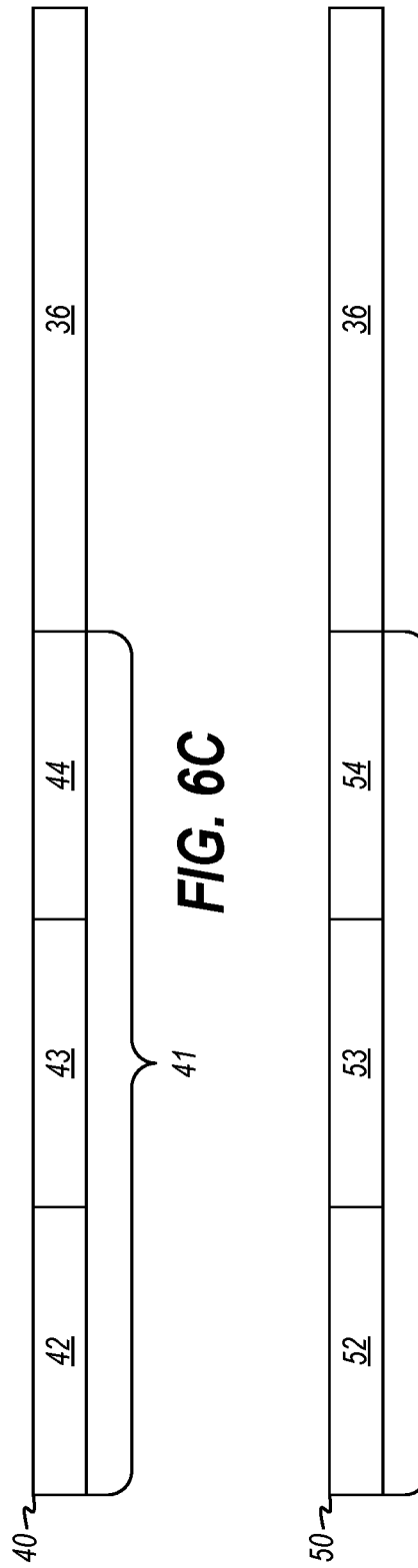
FIG. 6C is a data format diagram illustrating an exemplary IP packet format for transmitting a message payload from an eNB to a serving gateway (S-GW)
Figure 6D:
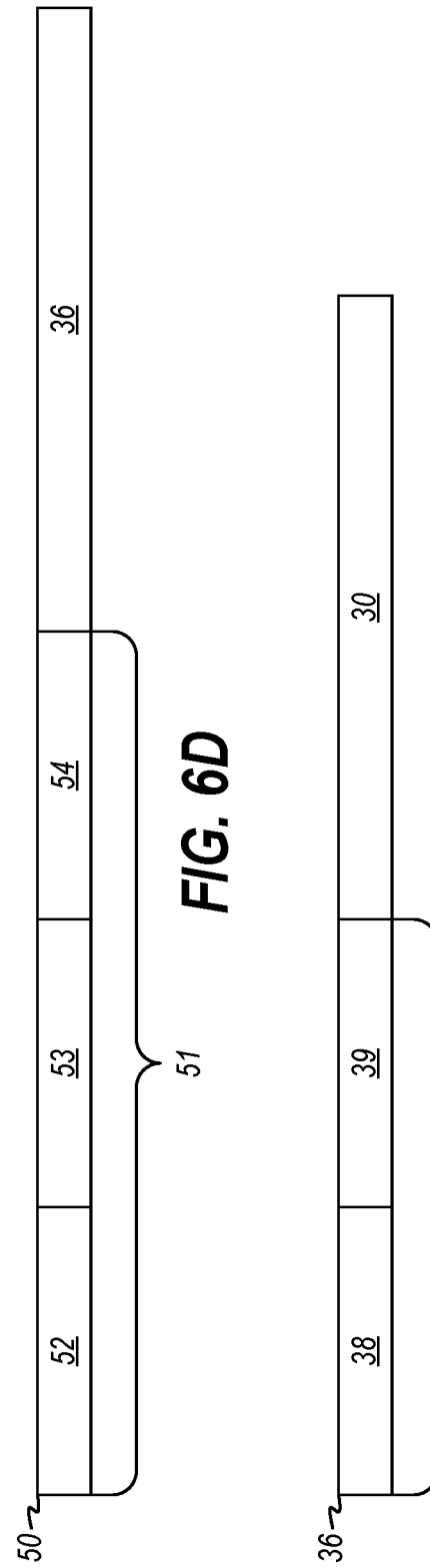
FIG. 6D is a data format diagram illustrating an exemplary IP packet format for transmitting a message payload from a S-GW to a Packet Data Network Gateway (P-GW)
Figure 6E:
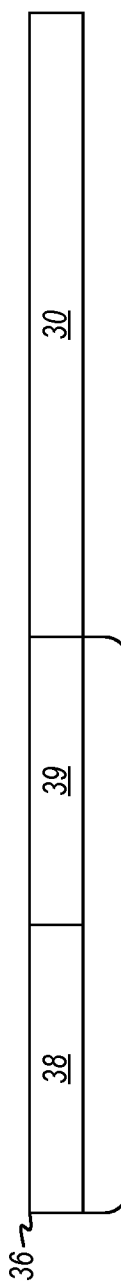
FIG. 6E is a data format diagram illustrating an exemplary IP packet format for transmitting a message payload from a P-GW to an Internet Packet Data Network.

FIG. 6B illustrates the format of an IP packet 36 transmitted from PEAD 2 to the nearest eNB 111a. As illustrated in FIG. 6B, the IP packet 36 includes an IP header 37 and the message payload 30. IP header 37 includes destination IP address 38 and source IP address 39. Destination IP address 38 is the IP address of the Internet-enabled personal emergency alert notification service 123. Source IP address 39 is the IP address of the PEAD 2. Using the LTE-Uu interface, the cellular modem of the PEAD 2 transmits each IP packet to the nearest eNB 111a via the DRB bearer set up for that particular PEAD 2. With reference to FIG. 6C, receiving eNB 111a receives each IP packet 36 and encapsulates each received IP packet with an S1 interface General Packet Radio System (GPRS) Tunneling Protocol (S1 GTP) header 41 to formulate an S1 GTP IP packet 40. The S1 GTP header 41 includes at least the destination IP address 42 of the destination Serving Gateway (S-GW) 114, the source IP address 43 as the IP address of the sending eNB, and an S1 Tunnel Endpoint Identifier (S1 TEID)) 44. The eNB then transfers the S1 GTP IP packet(s) 40 to a Serving Gateway (S-GW) via the S1 bearer via the S1 interface. With reference to FIG. 6D, the destination Serving Gateway (S-GW) 114 strips the S1 GTP header 41 from each S1 GTP IP packet 40 and encapsulates the stripped IP packet 36 into an S5 GTP IP packet 50, including an S5 interface GTP (S5 GTP) header 51. The S5 GTP header 51 includes at least the destination IP address 52 of the destination Packet Data Network Gateway (P-GW) 115, the source IP address 53 as the IP address of the S-GW 114, and an S5 Tunnel Endpoint Identifier (S5 TEID)) 55. The S-GW 114 then transfers the S5 GTP IP packet(s) 50 to the appropriate PDN Gateway (P-GW) 115 via the S5 bearer. The receiving P-GW 115 strips the S5 GTP header 51 from each packet 50 to extract the encapsulated IP packet 36 (FIG. 6E) and transfers the packet(s) onto the Internet 120 PDN via an SGi interface. Once the IP packet is on the Internet, it is routed to the destination IP address 38 of the personal emergency alert notification service 123 through conventional IP and/or Ethernet routing using TCP/IP and DHCP.

Referring again to FIG. 4, PEANS 123 may be implemented as software executing on a host computer system. In an embodiment, the PEANS 123 is accessible via the Internet. For example, PEANS 123 may be an application executing on a computer system that is accessible via a PEANS Server 122 via a web server 121 connected to the Internet 120. PEANS 123 may be a Cloud-based service that is hosted on an Internet-connected server such as an Amazon Web Services (AWS) server, available from Amazon, Inc. A PEANS web-enabled service may be an instance of a PEANS application executing in the Cloud, such as an E2C instance running on an Amazon Web Services (AWS) cloud web hosting platform. The computer system may be the same computer system executing the PEANS Server 122 or may be a separate computer system. In either case, the computer system may comprise at least one central processing unit executing PEANS program instructions stored in local or remote computer-readable memory. In an alternative embodiment, PEANS 123 may be a service that runs on a computer connected to an internal network of a closed network system.

Preferably, the PEANS 123 provides an Application Programming Interface (API) by which client devices access the PEANS 123. In an embodiment, the hosting computer system instantiates an instance of the PEANS 123 upon receipt of a proper API call to the PEANS 123. In other words, when a web browser or other software or another system generates a Uniform Resource Locator (URL) request containing the correct IP address of the hosting computer, along with the correct path to the directory containing the executable of the PEANS 123, and the API call is formatted correctly and contains valid parameters, the PEANS server automatically instantiates an instance of the PEANS 123.

Figure 7:
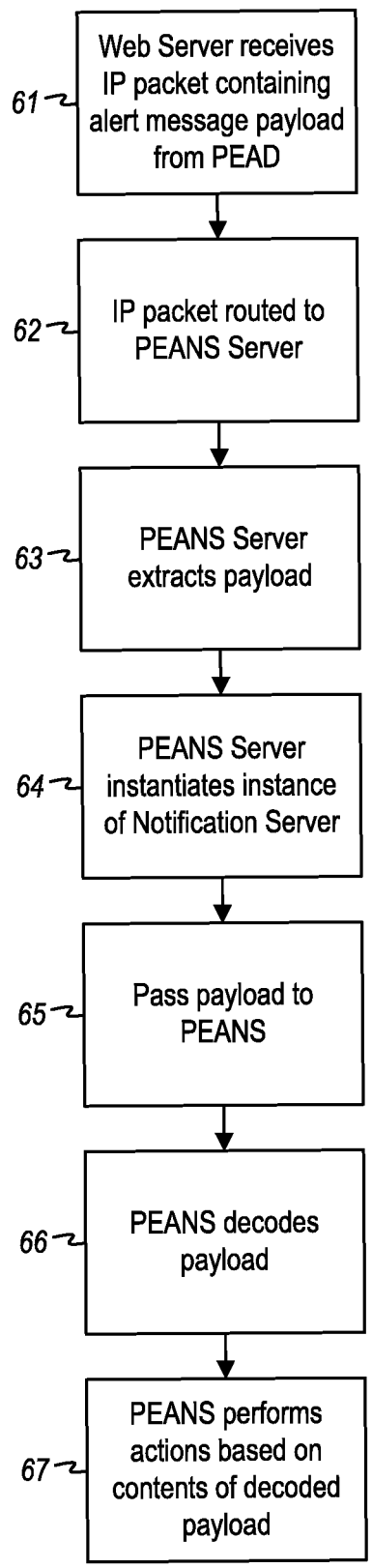
FIG. 7 is a flow diagram illustrating operation of an exemplary embodiment of a personal emergency alert notification service.

FIG. 7 is a flow diagram illustrating operation of an exemplary embodiment of the PEANS 123. As a preliminary step, a message in the form of an IP packet 76 containing the destination IP address of the PEANS Server 122 and a payload having the alert message contained therein is transmitted from the PEAD 2 over the LTE-M network 110 to a P-GW 115 and then over the Internet 120 to Web Server 121. The Web Server receives the IP packet (step 61), and then routes it to PEANS server 122 (step 62). PEANS server 122 extracts the payload of the received IP packet (step 63), and instantiates an instance of PEANS 123 (step 64), passing the payload 76 to PEANS 123 (step 65), via a PEANS API. PEANS 123 decodes the message payload 70 (step 66) and performs one or more actions based on the contents of the payload (step 67). In particular, PEANS 123 performs a series of appropriate steps according to predefined programming instructions. PEANS 123 performs one side of at least some of the Communication Sequence(s) executed in cooperation with the PEAD 2 controller 21 as described in connection with step 215 of FIG. 6. For example, it performs PEANS steps outlined in the Command Sequences, detailed hereinafter in connection with FIGS. 8A, 8B and 12.

In the system of FIG. 4, PEAD 2 is implemented with the following features: (1) operates on batteries to allow for portability; (2) uses very low power electronic components to conserve battery life; (3) uses power-saving techniques to conserve battery life; and (4) implements a LPWAN communication protocol to communicate to cellular base stations and passing of emergency alert messages to Internet-enabled notification service.

With regard to the batteries, in an embodiment, the main power source of PEAD 2/20 comprises battery supply 27 (see FIG. 2), such as lithium iron disulfide or alkaline battery non-rechargeable batteries. If desired, battery supply 27 may comprise rechargeable batteries, such as nickel metal hydride or lithium polymer batteries. In an embodiment, PEAD 20 may include an external charging system (not shown) to recharge the battery supply 27, such as an external power supply, a renewable energy source such as a solar cell, etc. Other battery technologies may be used without departing from the spirit and scope of the invention. In certain applications, PEAD 2 may be powered using conventional AC power, such as from a generator having a conventional AC power outlet, or even from a conventional AC power outlet supplied by a main power grid.

As mentioned above, PEAD 2 minimizes power consumption through use of low/very low/ultra low power components. By way of example and not limitation, and referring to FIG. 2, PEAD controller 21 comprises an ultra-low-power microcontroller unit (MCU) that consumes on the order of a few hundred microamps during normal operating mode, and on the order only a few microamps or less when operating in a power saving mode (PSM). In an illustrative embodiment, the MCU comprises a STMicroeletronics STM8L151C8 microcontroller with integrated flash memory and EEPROM which consumes 20 microamps in normal operating mode and less than 6 microamps when placed in a low power mode. By further way of example and not limitation, communications module 23 comprises a Quectel LPWA Module BG96, manufactured by Quectel Wireless Solutions Co., Ltd., headquartered in Shanghai, China. The Quectel BG96 Cat.M1/NB1 & EGPRS Module includes a cellular modem that is capable of signal transmissions using either CAT-M1 or CAT-NB1 (NB IoT) protocols over existing LTE/Extended GPRS (EGPRS) networks. The Quectel BG96 consumes a mere 10 microamps when operating in power saving mode and 190 mA when transmitting at full strength of 23 dBm. The Quectel BG96 is programmed to use CAT-M1 protocol when connecting to an LTE-M cellular network, and is programmed to use CAT-NB1 protocol when connecting to an NB-IoT enabled cellular network. Further in an embodiment and by way of example and not limitation, PEAD activation sensor(s) 26 may be implemented using MEMS sensors, where appropriate. For example, in an embodiment, microphone sensor 26 comprises a STMicroelectronics MP34DT05-A MEMS audio sensor.

PEAD 2 minimizes power consumption through use of power saving techniques. Several PEAD 20 components (such as controller 21, signal processor 29, communications module 23 and geolocation module 24) are capable of being placed in a power saving mode (PSM), whereby certain high(er)-power consumption features of components are shut down and/or placed in a sleep mode when placed in PSM. For example, the communications module 23 turns off power to the antenna 23*a* when in PSM. The selection of the communications module 23 must of course consider the network over which alert messages are to be transmitted to ensure that the communications module 23 is capable of transmitting according to the protocol required by the selected network.

Power efficiency and conservation may be further achieved through power-saving communication methodologies. For example, a PEAD 20 may not connect to the network at all until it is activated. In implementations that do require PEAD 20 to check in (in order to verify that the PEAD 20 is still operational), PEAD 2 may check in to the network/notification service based on infrequent intervals. Once activated, it is generally desirable to maintain a connection to PEANS; however, further power conservation may be achieved by placing components in PSM between geolocation capture intervals.

PEAD 2 implements a LPWAN communication protocol to communicate to cellular base stations and passing of emergency alert messages to Internet-enabled notification service. For example, in the ille PEAD 2 implements LTE-CAT-M1 protocol to communicate with the cellular network 110 for further routing to Internet-enabled Notification Service 123. LTE-CAT-M1 specifies a transmission signal strength of 23 dBm.

Figure 8A:
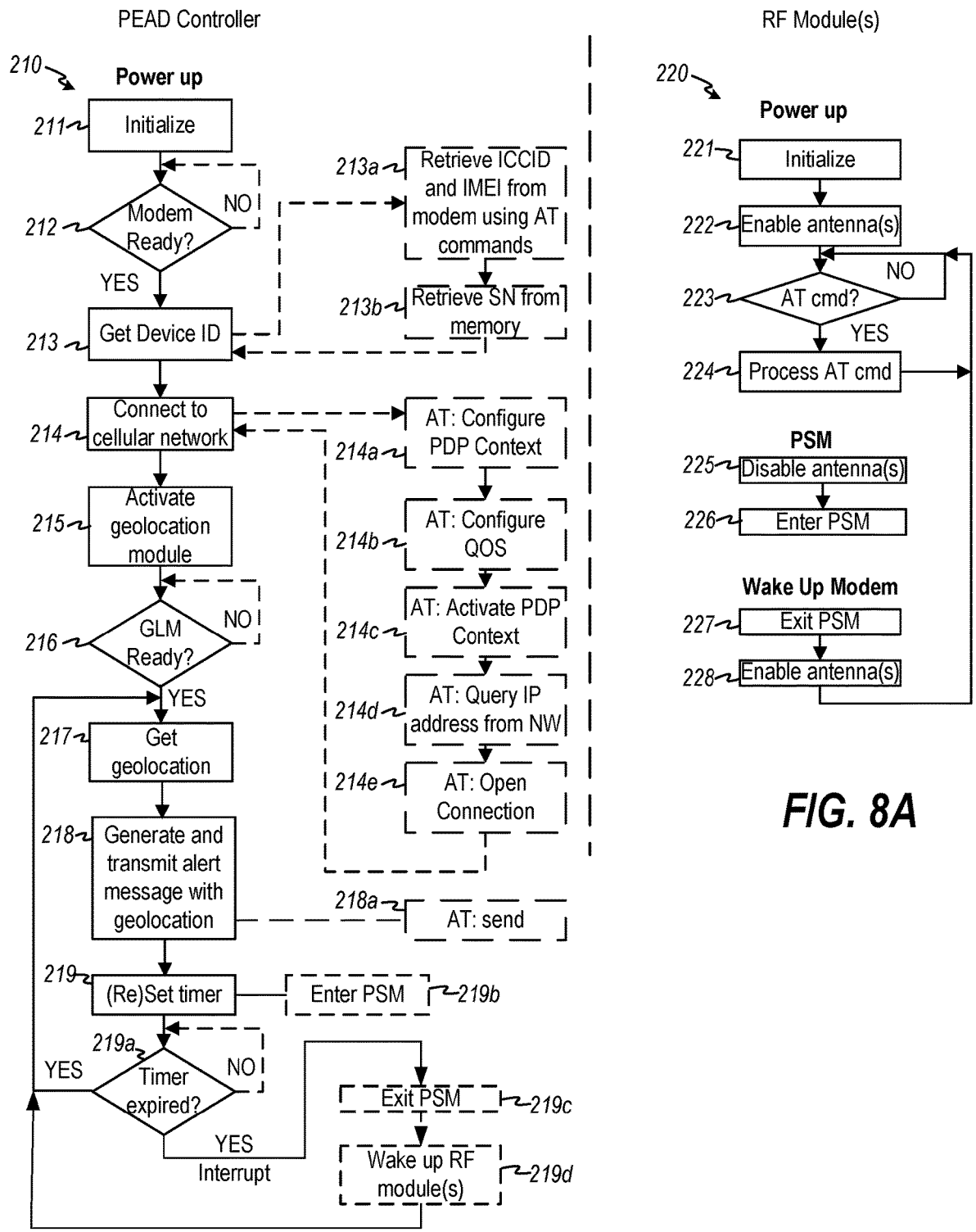
FIG. 8A is a flowchart illustrating an exemplary operation of an embodiment of a personal emergency alert device implemented to activate upon power-up of the device.

FIG. 8A is a flowchart illustrating an exemplary operation 210 of the PEAD 2. As shown, in operation, when the PEAD 2 is powered on, for example by turning on a power switch 28, the controller 21 and communications module 23 (and optionally the geolocation module 24) (each, and together, RF modules), each perform an initialization (steps 211 and 221). Once the controller 21 is initialized, it waits for the modem to be ready (step 212). In an embodiment, the controller 21 monitors the Ready status (typically the output state of an output port, pin or pad on the cellular modem) of the communications module 23. At first power the communications module 23, and optionally the geolocation module 24, each perform an initialization (step 231), enabling its antenna(s) 23*a*, 24*a* for signal transmission and/or reception (step 222). In an embodiment, once initialized, the communications module 23 is a cellular modem and signals its "ready" status by enabling a Ready pin on the modem.

Once the communications module 23 is ready to transmit and/or receive, the controller 23 obtains the device identifier (step 213). In an embodiment, the device identifier comprises the serial number of the PEAD 2. In alternative embodiments, the device ID may comprise alternative and/or additional identification information, such as but not limited to the ICCID, and the IMEI of the PEAD 2 (or components thereof). In an embodiment, the ICCID is integrated into the SIM 25, and the controller 23 instructs the communications module 23 to access the SIM 25 to obtain the ICCID of the SIM 25 (step 213*a*). In an embodiment, the IMEI is programmed into an Electrically-Erasable Programmable Read-Only Memory (EEPROM) embedded in the communications module 23, and the controller 23 issues a command to the communications module 23 to obtain it (step 213*a*). In an embodiment, the manufacturer of the PEAD 20 issues a unique serial number for each PEAD module at the time of manufacture, and stores it in a Programmable Read-Only Memory (PROM) or other memory 22, accessible and accessed by the controller 21 (step 213*b*).

Once the device ID is obtained, the controller 21 then instructs the communications module 23 to connect to the subscriber cellular network 110 (FIG. 4) (step 214). The communications module 23 is programmed to recognize various AT commands, which are commands to control communication using the modem 23. In an embodiment, the communications module 23 is configured with an embedded TCP/IP protocol stack, and the AT commands are translated into messages/responses, encapsulated into TCP/IP packets and transported over the cellular network 110 according to TCP/IP protocol. In an embodiment, the controller 21 instructs the communications module 23 to connect to the subscriber cellular network 110 by (1) configuring a Packet Data Protocol (PDP) Context with the network Access Point Name (APN), the subscriber name, password and authorization type (step 214*a*), (2) configuring the Quality of Service (QoS) settings (step 214*b*), (3) activating the PDP Context (step 214*c*), (4) querying the network for the IP address of the PDP context (step 214*d*), and (5) opening the connection (step 214*e*). Once the connection is open, the PEAD 2 is able to send and/or receive requests, commands, responses and data (step 215) to/from PEANS 107. In an embodiment, the send/receive step 215 may include sending device status, alerts relating to received sensor information, location information, and communication acknowledgements to PEANS 107, and receiving communication acknowledgements, messages, or settings or firmware updates from PEANS 123.

Once connected to the cellular network, the controller 21 then activates the geolocation module (step 215), if it is not automatically self-activated at power up. The controller monitors the geolocation module (step 216) to determine when it is ready for use. In an embodiment, the geolocation module is a Global Positioning Signal (GPS) transceiver that includes an output port, pin or pad on through which it indicates is "ready" status. Once the geolocation is ready for use, controller 21 then obtains the current geolocation information of the PEAD 2 (step 217), for example by sending a request to the GPS transceiver. Controller 21 then generates an alert message and instructs the cellular modem 23 to transmit the alert message to PEANS 3 (step 218). In an embodiment, controller 21 sends a sequence of AT send commands to the cellular modem 23 (step 218). Controller then sets (or resets) a timer (step 219) to wait a predefined time interval, waits until the timer expires (step 219*a*, and then repeats steps 217-219*a* until the battery level depletes.

In an embodiment, controller 21 may utilize power saving techniques by basing a controller interrupt input on the output of the timer. In this embodiment, when the controller 21 sets the timer (step 219), it places itself and the RF module(s) into a power saving mode (PSM) (step 291*b*). Then, when the timer expires, it generates an output signal that is connected to an interrupt input on the controller 21. When the timer generates an interrupt of the controller 21 upon expiration of the timer (step 219*a*), the controller 21 exits PSM (step 219*c*) and wakes up the RF module(s) (step 291*d*).

Figure 8B:
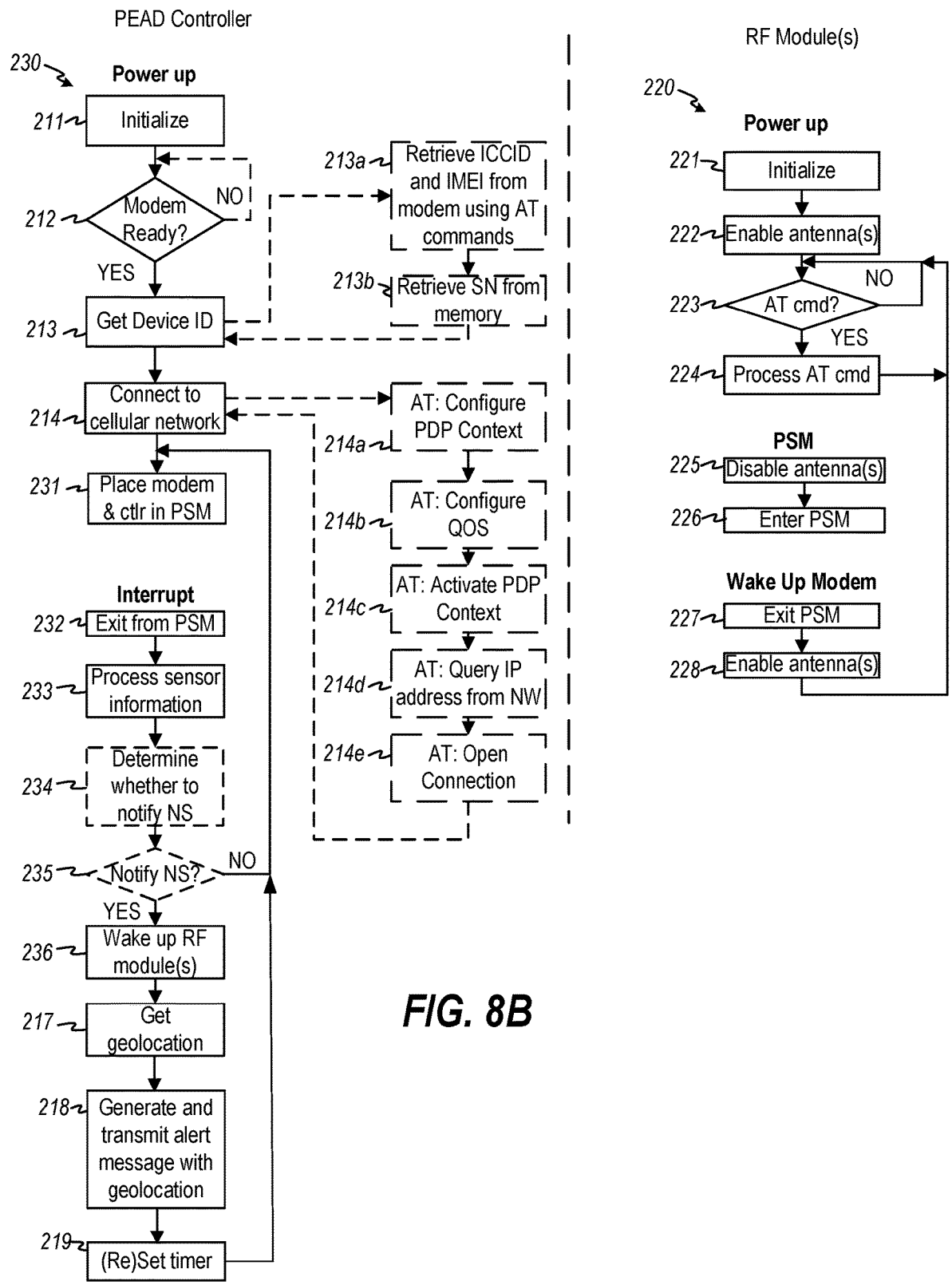
FIG. 8B is a flowchart illustrating an exemplary operation of an embodiment of a personal emergency alert device implemented to establish radio bearers upon initial power up and then enter low-power mode until a sensor detects an emergency activation condition.

FIG. 8B illustrates an alternative embodiment of the operation of PEAD 2, wherein instead of using the initial powering on of the PEAD 2 as the activation alert, the PEAD 2 is instead first powered up to pre-register with the network 10 and PEANS 3 to set up bearers (data tunnels) so that if an when PEAD 2 is activated via its activation sensor(s) 26, it can immediately send the alert message. Referring to FIG. 8B, in this embodiment, the controller and RF module(s). In FIG. 8B, PEAD 2 executes steps 211-214 as previously described in connection with FIG. 8A. Once a connection to the network 10 and PEANS 2 has been established, controller 21 places itself and the RF module(s) in PSM (step 231). In an embodiment, PEAD 2 remains in PSM until it is activated via one of the sensors 26. In an embodiment, controller 21 comprises a microprocessor having one or more interrupt input port(s) connected (directly or indirectly) to output port(s) of activation sensor(s) 26. When an activation sensor 26 detects an activation condition, it generates an interrupt on controller 21. When controller 21 is interrupted by sensor(s) 26, it executes an interrupt service routine in which it exist from PSM (step 232), processes the alarm signal to extract sensor information (step 233), optionally determines whether it should notify the PEANS 3 (step 234) (for example, if PEANS 3 has previously been notified and alert messages are being sent too frequently), and if it determines it should notify the PEANS 3 (as determined in step 235), it wakes up the RF module(s) 23, 24 (step 236), and then retrieves the geolocation information (step 217), generates and transmits an alert message containing geolocation information to PEANS 3 (step 218), (re)sets the timer (step 219), and returns to step 231 to place itself and RF module(s) 233, 234 back in PSM. The operation of the RF module(s) is the same as in FIG. 8A.

Figure 9:
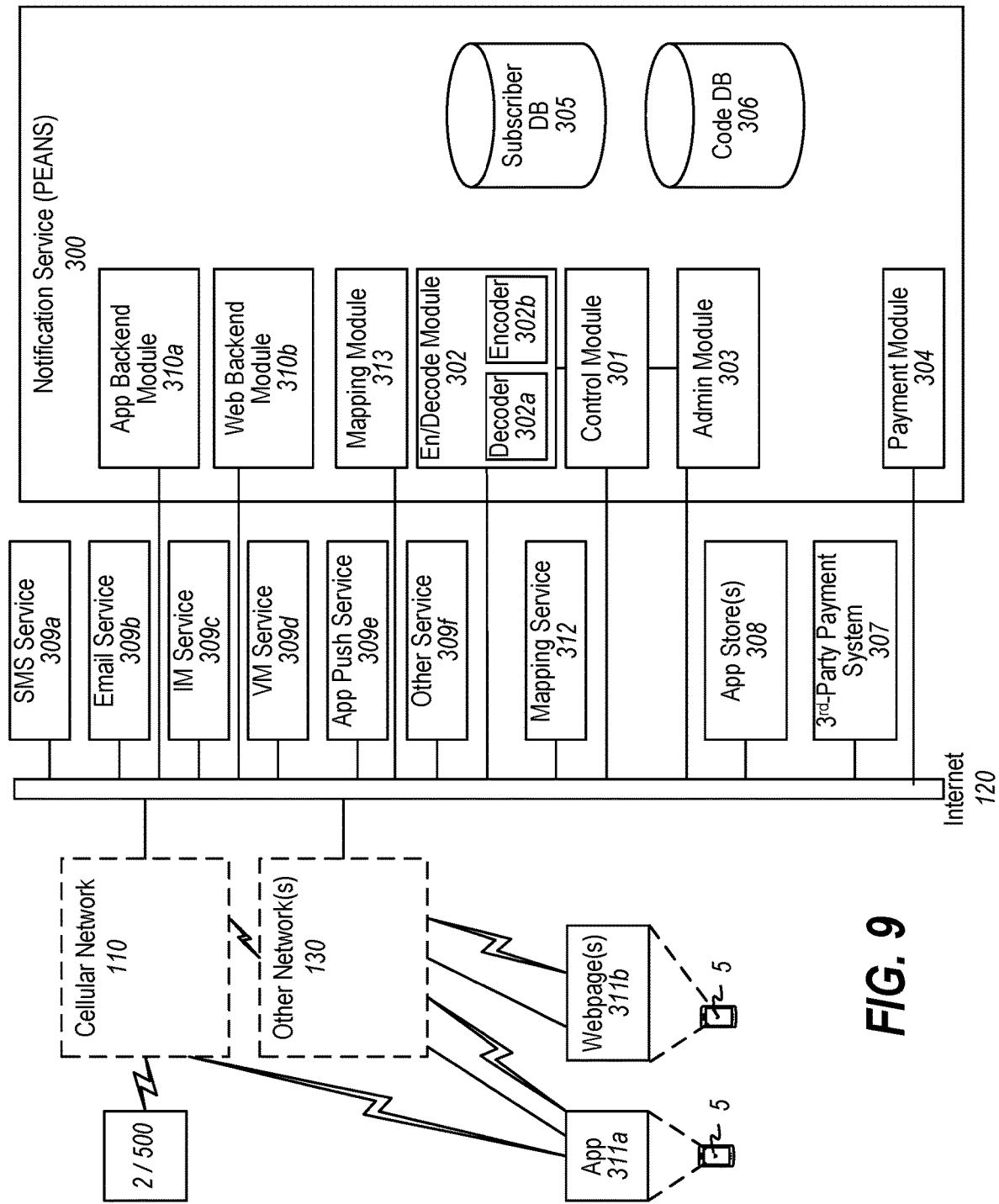
FIG. 9 is system diagram of a networked environment and illustrating an architectural block diagram of an embodiment of the personal emergency alert notification service.

FIG. 9 shows a more detailed diagram of the architecture of an embodiment 300 of personal emergency alert notification service (PEANS) 123. As shown therein, PEANS 300 includes a central control module 301, an encode/decode module 302, an administrative (Admin) module 303, a payment module 304, an App Backend module 310, a Mapping Module 313, a subscriber database 305, and a code database 306. Each of the modules comprises computing resources and computer-readable storage memory. For example, each module may comprise a service or application or program comprising program instructions and executed by one or more processor(s) such as Central Processing Unit(s) (CPU), microprocessor(s), cloud computing resource(s) (such as an Amazon Web Service E2C instance(s)), etc. Each database 305 and 306 comprises computer-readable storage memory and may be implemented as a managed system (DBMS), local storage, Amazon Web Services S3 bucket(s), etc. PEANS 300 is connected to the Internet 120 through which it may communicate with one or more 3$^{rd}$-party payment systems 307, App Store(s) 308, and services 309a-309f and 312.

Encode/decode module 302 (and specifically the decoder portion, or "decoder," 302a of encode/decode module 302) decodes messages received from remote PEAD modules 5 that are routed to it from PEAD 2 through the Internet 120 (for example, from the P-GW 115 (FIG. 4) of the cellular network 110). Decoded messages are passed from encode/ decode module 302 to control module 301 whereby control module 301 processes the decoded message in accordance with predefined instructions as set forth herein. In an embodiment, the decoder 302a decodes the message payload 30 to extract the device ID from the device ID field 32 (FIG. 6A) of the message payload 30, which is used by the control module 301 to identify the PEAD 2 that sent the message. Additionally, the decoder 302a may extract the contents of additional fields 33, 34, 35 (FIG. 6A) from the message payload 30 to be used by the control module 301 to determine and execute the appropriate command sequence in connection with the message received from the PEAD 2.

The encode/decode module 302 (and specifically the encode portion, or "encoder", 302b of the encode/decode module 302) also encodes messages and data to be sent from PEANS 300 to the PEAD 2. Specifically, the encoder 302b encodes into a packet payload information that is to be transmitted from the Notification Service to the PEAD 2. The encoder 302b formats the packet payload in a format that is decodable by the PEAD 2, and then encapsulates the packet payload into one or more IP packets for routing to the PEAD 2 via the Internet 120 and cellular network 110.

The central control module 301 operates as the central controller for PEANS 300 and offers one or more Application Programming Interface(s) (APIs) to allow other modules, services and devices connected to the Internet 120 to communicate with PEANS 300.

Admin Module 303 may provide code management tools which allow an administrator to manage app and firmware versions, and deployment of app and/or firmware upgrades to electronic devices 5 and/or PEADs2. In an embodiment, Admin Module 303 may be configured to allow a vendor or manufacturer of a device that incorporates PEAD 2 to keep track of firmware versions of its respective devices in the field, and control deployment of firmware upgrades to such devices.

The code database 306 comprises computer-readable storage memory and stores one or more versions of firmware for the PEADs 2, one or more versions of apps for the App Store(s) 308, and other administrative data, program data, and information. For example, the code database 306 may include app code and various versions thereof of an app 311a that may be downloaded to an app store 308 and made available to subscribers to PEANS 300. For example, PEANS 300 may make available one or more apps such as an iOS app for Apple devices such as iPhones and iPads, and an Android app for Google Android devices. These apps may be made available through the Apple store or Google Play store. A subscriber may download an available app 311a from one of the stores 308 The apps may be downloaded and installed by an end user from one of the Apple store of the Google Play store to their end user electronic device 5. The app 311a communicates with PEANS 300 using conventional app technology such as made available through the electronic device operating system (such as iOS or Android).

Admin Module 303 may also provide tools to allow an administrator to access profiles, account information and/or subscriber records of subscribers of the PEANS 300. These tools may include graphical user interfaces, controls and/or methods for setting up subscriber accounts, creating subscriber records, and adding, activating, modifying, and/or removing subscriber profiles, subscriber accounts, and/or subscriber records. For example, Admin Module 303 may include a Customer Support tool (not shown) that allows a customer service representative to assist subscribers of the personal emergency alert notification service, including allowing such customer service representative to add, remove, and/or modify information contained in a subscriber record 360 (FIG. 10) stored in the Subscriber database 305.

Figure 10:
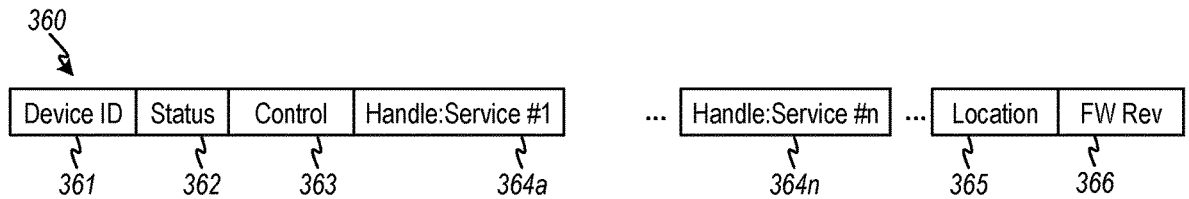
FIG. 10 is a data format diagram illustrating an exemplary embodiment of a subscriber record stored in a subscriber database.

FIG. 10 illustrates an example format of a record 360 stored in the Subscriber Database 305. Each record 360 is associated with a registered PEAD 2 and includes a plurality of fields 361, 362, . . . , 366 containing information about (1) the subscriber, (2) the respective PEAD 2, and (3) notification service configuration(s). In an embodiment, each record 360 includes a field 361 containing a device identifier that uniquely identifies the registered PEAD 2. Each record 360 also includes field(s) 364a, . . . , 364n, that contain (either directly or indirectly using a pointer or indirect reference to) one or more notification recipient delivery service handles (username, phone number, user or device identifier, etc.) and corresponding delivery services (e.g., email, SMS text, in-app push notifications service) through which a message can be delivered to one or more person(s) corresponding to such handle(s). Each record 360 will also typically include additional fields, such as but not limited to status fields 362 indicating various status information about the PEAD 2, control fields 363 used to trigger certain remote maintenance and/or control configuration and behavior of the remote PEAD 2. The record 360 may also include one or more location-related field(s) 365, which may include such location information as most recent GPS coordinates, a log of recent GPS coordinate, and/or user-identified location description (for example an ASCII text description of the location that indicates the location of PEAD 2). The record 360 may further include one or more firmware version field(s) 366.

Generally at least one record 360 is stored for each PEAD 2 monitored by the PEANS 300. A typical subscriber database 305 will store thousands of PEADs or hundreds of thousands of PEADs or more records, corresponding to unique PEAD modules 2.

Figure 11:
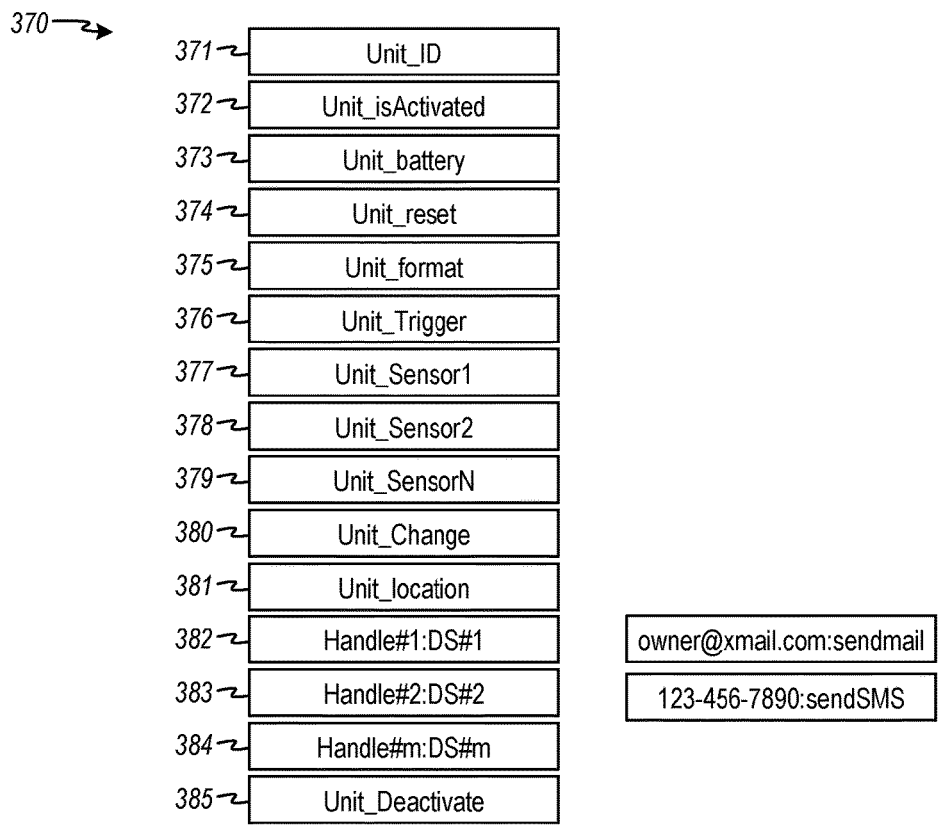
FIG. 11 is a data format diagram illustrating in more detail an exemplary embodiment of a subscriber record stored in a subscriber database.

FIG. 11 illustrates an example subscriber database record 370 with illustrative contents. As illustrated, the example subscriber database record 370 includes the following fields: Unit_ID 371, Unit_IsActivated 372, Unit_battery 373, Unit_reset 374, Unit_format 375, Unit_Trigger 376, Unit_Sensor1 377, Unit_Sensor2 378, Unit_SensorN 379, Unit Change 380, Unit_location 381, Handle #1 382, Handle #2 383, Handle #m 384, and Unit_Deactivate 385. The format of handles 382, 383, 384 may include a handle name and a delivery service name. For example, Handle #1 382 may be an email address (e.g., owner@mail.com) and a corresponding email delivery service (e.g., "sendmail"). As another example, Handle #2 383 may be a phone number (e.g., "123-456-7890") and an SMS text delivery service name (e.g., "sendSMS").

Referring again to FIG. 9, PEANS 300 may also include an App Backend Module 310a and/or a Web Backend Module 310b, each of which respectively operates as an interface between PEANS 300 and instances of end user Apps 311a or Web page(s) 311b displayed in a browser, executing on end users' electronic devices 5. Subscribers to PEANS 300 may interact with PEANS 300 via (1) a downloadable App 311a running on an Internet-enabled electronic device 5 (such as but not limited to a smartphone, a tablet or laptop, a desktop computer, a terminal connected to a server or other computer, etc.), and/or (2) via one or more Web page(s) 311b running in a Web browser executing on a computer system or mobile device. The app 311a may be downloaded to the user's device 5 from an Internet-enabled device-accessible App store 308, such as the Apple App Store, Google Play, or other App stores through which apps can be selected and downloaded. Apps may be provisioned in the App stores 308 from the code database 306. The app 311a runs locally on the user's device and is supported by the App Backend Module 310a so as to effectuate communication, collection of user input, and display of information relating to the end user's account and subscriber devices (i.e., PEADs 2 registered to the subscriber account). Alternatively, a subscriber may access the PEANS 300 via a web portal such as a website that provides subscriber access and a graphical user interface (GUI) on one or more Web page(s) 311b displayed within in a web browser running on a computer or other electronic Internet-enabled device 5, and which allows a subscriber to interact with the PEANS 300 via a Web Backend Module 310b. Hereinafter, the detailed description refers frequently to an app 311a or apps 311a. It is to be understood that the functionality described herein with respect to such app or apps 311a may alternatively or additionally be implemented as webpage(s) 311b in communication with the Web Backend Module 310b.

Control Module 301 provides an API through which user apps 311a can communicate with PEANS 300 and configure their user profile, notification recipient information, and the operational settings for their registered PEAD 2. Users connect to PEANS 300 through the app 311a running on their local device 5, which connects to the Internet directly through WiFi, a LAN (via Ethernet), and/or indirectly through a cellular or other network 130. Communication between the app 311a and control module 301 are routed using conventional TCP/IP over the Internet 120 and/or cellular networks. The app 311a provides prompts radio buttons and/or other graphical user interface (GUI) widgets/controls to allow the user to configure settings for the PEAD 2 and for operation of PEANS 300 relative to the particular PEAD 2. As an example, the app 311a may provide a GUI displaying a slider that allows a user to set the level of sensitivity of a sensor on the PEAD 2. Changing the sensitivity level changes the sensitivity level of a sensor to a type of event and may result in more or fewer activation conditions sent to the PEAD module controller based on the sensitivity setting.

When a user or owner of a PEAD 2 subscribes to PEANS 300, the user enters the subscriber information, including subscriber details such as contact information, notification recipient information including delivery service handles and associated delivery services to use to notify notification recipients, and payment information. During registration with PEANS 300, the user may be required to submit a payment for subscribing to the services. Accordingly, PEANS 300 may also include a Payment Module 304. The Payment Module 304 may either manage payment from a subscriber directly, or may handle communication with a $3^{rd}$-party payment processing system 307 to process payments.

Control module 301 is configured to receive an alert message (e.g., an IP packet containing the message payload 30 (FIG. 6A)) from PEAD 2, extract the payload 30 (including the alert message) from the IP packet, extract the device ID 31 from the payload, decode the alert message 33, and optionally determine whether the alert requires generation of a notification to one or more notification recipients. If a notification is required, the control module 301 accesses the record 360 associated with the PEAD 2 from the subscriber database 305 to look up the notification recipients and corresponding delivery handles and associated delivery services 364a, 364b, 364n, formats messages appropriate to the particular delivery services and sends the message(s) to the respective delivery services via the Internet 120. Each delivery service includes an Internet-enabled delivery service running on computer systems or other hardware that is connected to, and accessible via, the Internet 120. For example, and again referring to FIG. 9, PEANS 300 may utilize the service(s) of one or more SMS text services 309a, one or more email services 309*b*, one or more instant messaging services 309*c*, one or more text-to-voice or other voice mail messaging services 309*d*, one or more app push notification services 309*e*, and one or more other Internet-enabled messaging services 309*f*. Such services adhere to conventional TCP/IP protocols for passing messages thereto.

In an embodiment, the Encoder/Decoder module 302 in FIG. 9 is the initial point of entry to PEANS 300 of messages issued from PEAD 2 and is the exit point from PEANS 300 for messages going to PEAD 2. Each alert message contained in the payload 30 of the IP packet 36 (FIG. 6E) coming from PEAD 2 is in an encoded format, for example as discussed in connection with FIGS. 6A and 6E. The decoder 302*a* of the Encoder/Decoder module 302 extracts the message payload 30 (FIG. 6A) from the IP packet 36 (FIG. 6E) and decodes the message payload bits into a format or other data usable by the control module 301. Based on the decoded information generated by the decoder 302, the control module 301 performs one or more actions, as described in connection with FIG. 12.

Generally, PEAD 2 only contacts PEANS 300 for one of two reasons: (1) to alert the PEANS 300 of the occurrence of an emergency event at the PEAD 2, or, in an optional embodiment, (2) to check in with PEANS 300 to indicate that the PEAD 2 is still functioning and connected (also referred to herein as the "heartbeat" function).

Figure 12:
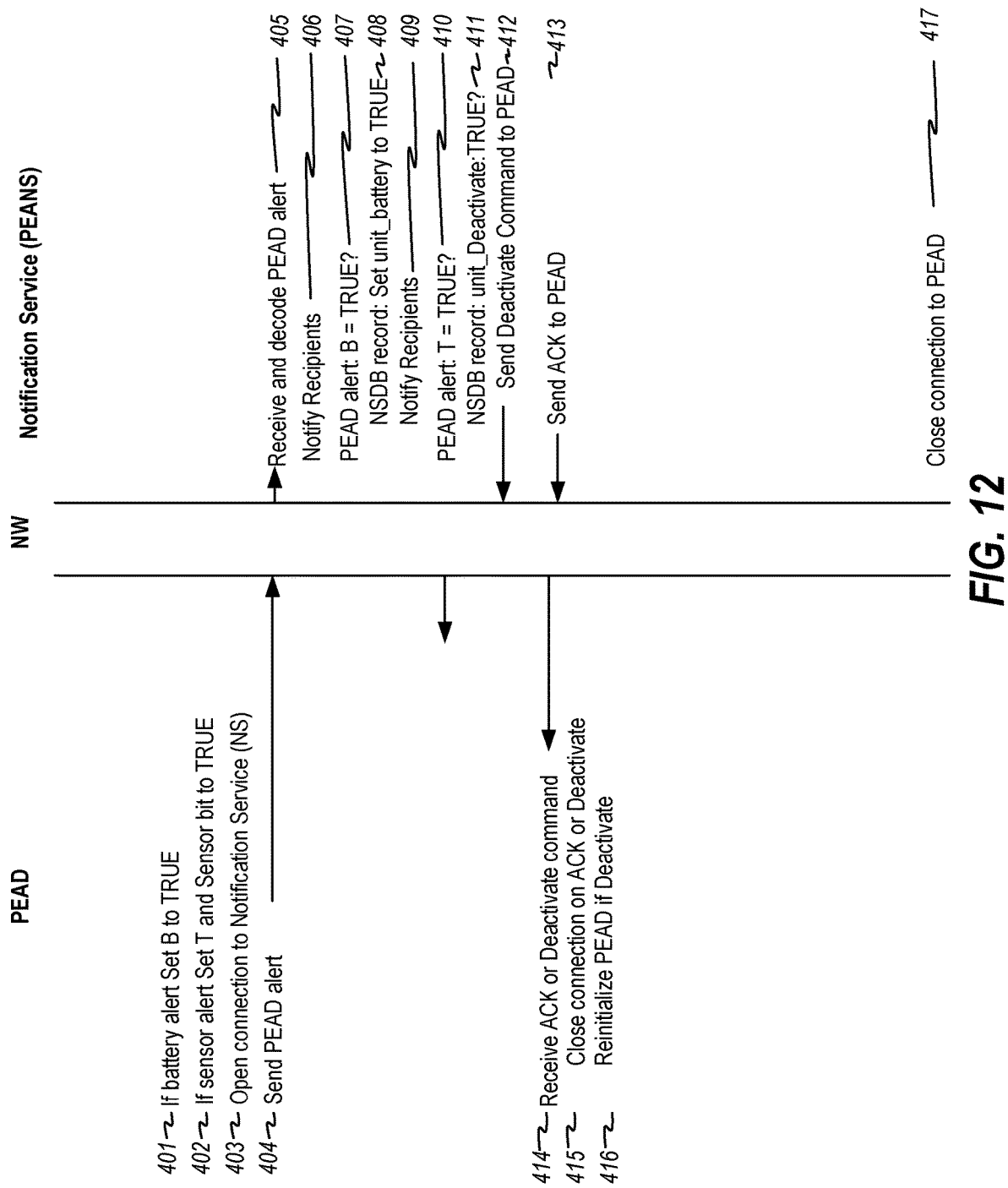
FIG. 12 is a communications diagram illustrating an exemplary embodiment of the communications operations between a personal emergency alert device and the personal emergency alert notification service.

FIG. 12 is an interaction diagram illustrating an example operational implementation of the actions of, and communications between, PEAD 2 and PEANS 300. The actions in FIG. 12 illustrate in more detail certain actions that may ensue after the PEAD 2 has been initialized and has established a connection to the cellular network. FIG. 12 illustrates an example implementation of the steps PEAD 2 may take when it receives an alert from a monitored sensor or a device-based user input such as activation of a power switch or button. In an embodiment, such events cause the controller 21 in the PEAD 20 to wake up from a low power state, process the sensor information and, if determined that an alert message should be sent, generate and send an alert message to PEANS 300 (see FIGS. 8A and 8B).

As illustrated in FIG. 12, upon receiving a sensor alert, PEAD 2 determines the source of the sensor alert. If it is a battery low alert, controller 21 sets a battery status bit B in field 34 (FIG. 6A) to true (step 401). If the alert is due to an activation sensor 26, controller 21 sets the trigger bit T in field 34 to true and if PEAD 2 includes more than one activation sensor 26, sets to true a bit S1, S2, . . . , Sn in alert field 33 corresponding to the triggered sensor (step 402). Controller 21 then opens a connection to the PEANS 123 (step 403) and sends the alert message to PEANS 300 (step 404).

On the PEANS 300 side, PEANS receives and decodes the alert message from PEAD 2 (step 405). PEANS notifies the notification recipients (step 406). If the alert message indicates the battery is low (step 407), PEANS updates the Unit_battery bit 373 in the database record corresponding to the sourcing PEAD 2 to reflect the low battery condition (step 408), and optionally notifies the notification recipients (step 409). If the alert message indicates an emergency alert message, (step 410), PEANS 300 checks the Unit_Deactivate bit 385 in the database record corresponding to the sourcing PEAD 2 to see if the PEAD 2 should be deactivated (for example, in the situation that PEANS 300 received a valid deactivation code, per FIG. 3B) (step 411). If the PEAD 2 should be deactivated (i.e., the Unit_Deactivate bit 385 is set), PEANS 300 sends a Deactivate command to PEAD 2 (step 412); otherwise it sends an acknowledge handshake (ACK) (step 413) and closes its connection to PEAD 2 (step 417).

PEAD 2 receives either an ACK or Deactivate command (step 414). In either case, PEAD 2 closes the connection to PEANS 3 (step 415). If the response is a Deactivate command, PEAD 2 reinitializes the PEAD 2 to reset it and thereby deactivate its present emergency alert status.

Hub Embodiment

Figure 13:
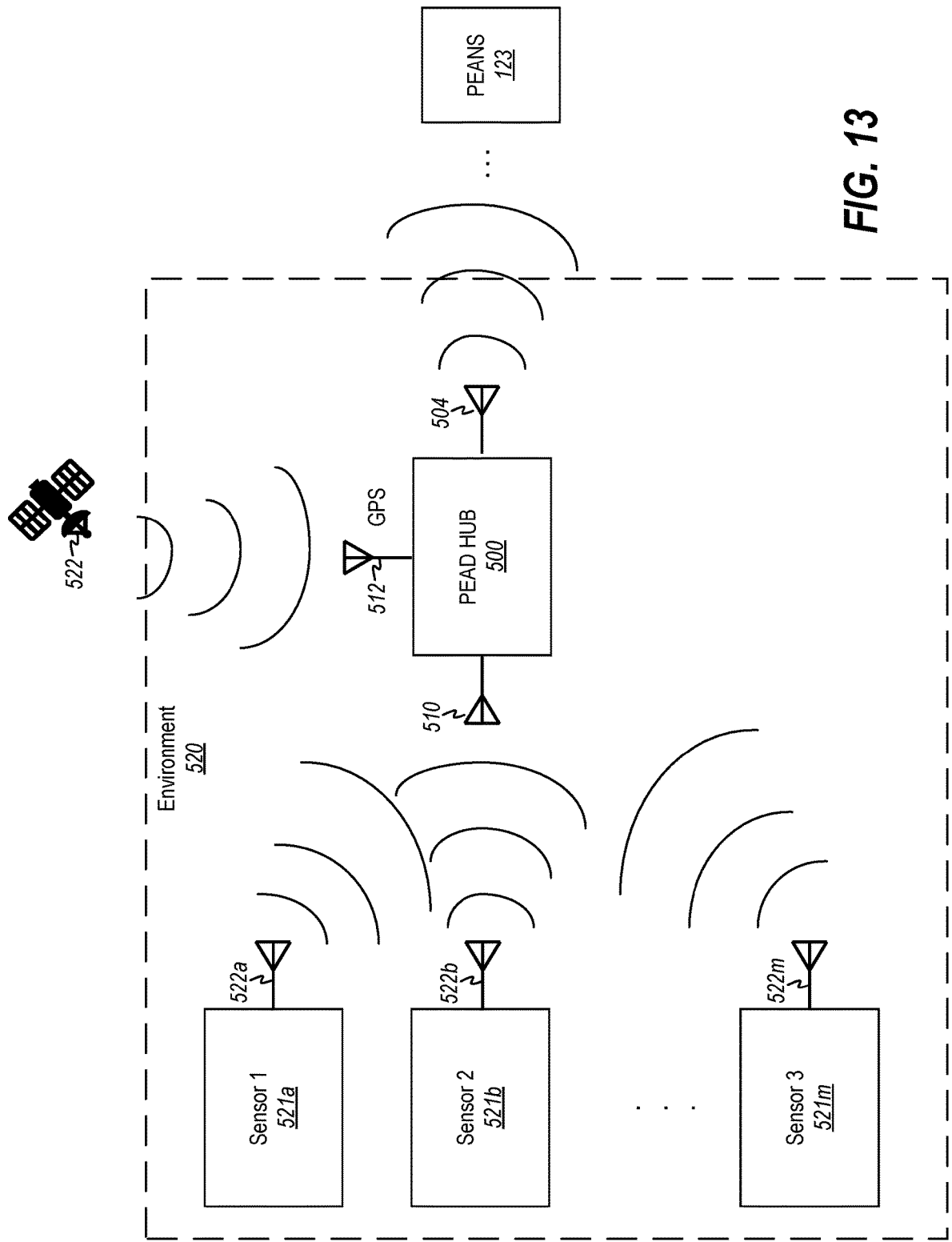
FIG. 13 is a system diagram illustrating a personal emergency alert device hub system in communication with remote activation sensors.

It will be appreciated that a more expansive AED tracking system can be implemented using a hub concept. FIG. 13 is a block diagram of an embodiment of a system in which a PEAD 500 is a communications hub, or PEAD hub. PEAD hub 500 serves as a hub to one or more remote sensors 521*a*, 521*b*, 521*m* situated within an environment 520 in wireless communication range of the hub 500. Each sensor 521 has itself, or has shared with other sensor(s) 521, a wireless transmission capability, such as a controller, modem and antenna, for transmitting a sensor alert signal via a sensor antenna 522*a*, 522*b*, . . . , 522*m* upon detection of a sensor trigger condition.

Figure 14:
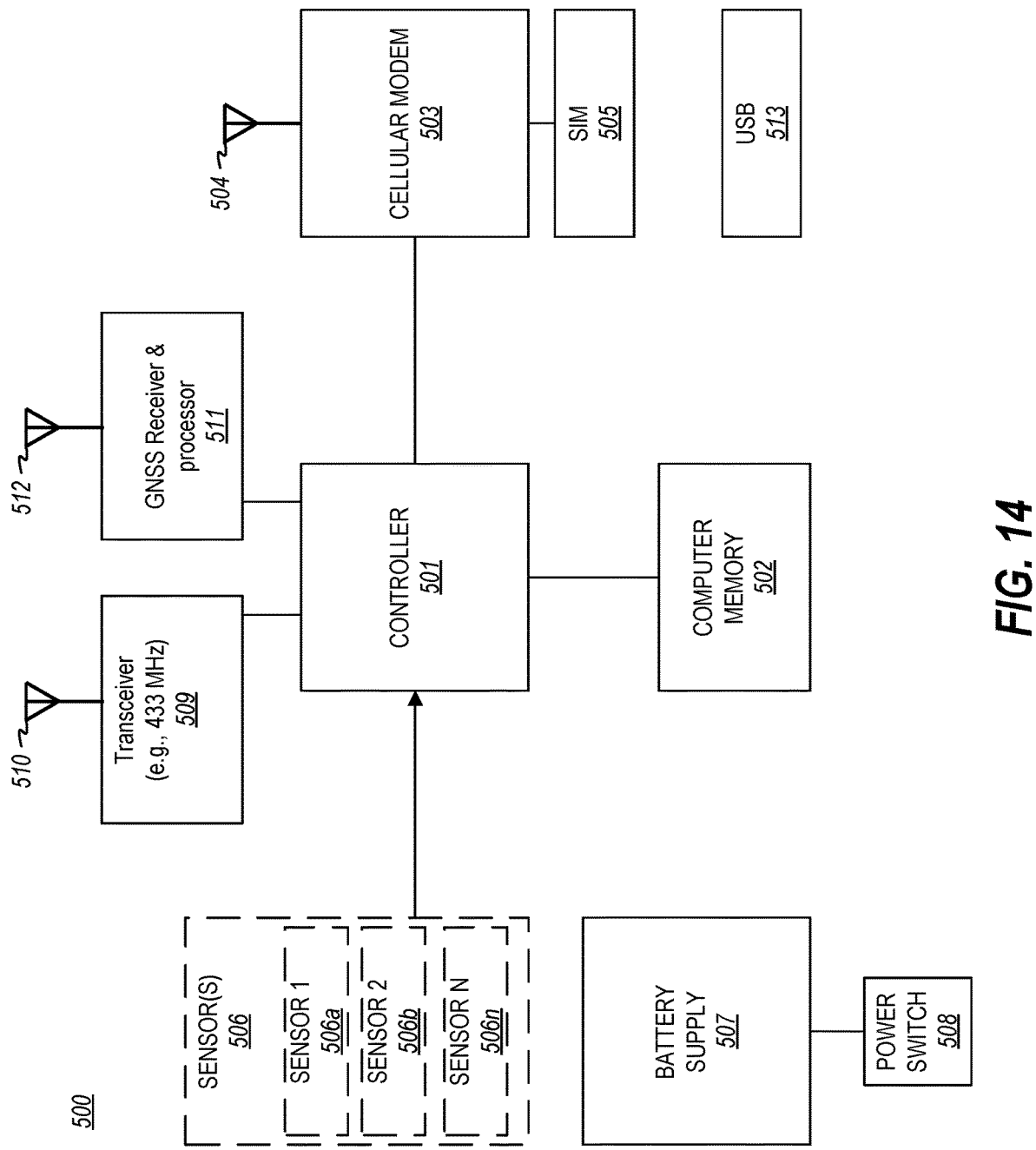
FIG. 14 is a block diagram illustrating an exemplary embodiment of the personal emergency alert device hub of FIG. 13.

FIG. 14 is a block diagram of an embodiment of a PEAD hub 500. In this embodiment, PEAD hub 500 includes a controller 501, computer readable storage memory 502, a cellular modem 503 with antenna 504, a Subscriber Identification Module (SIM) 505, a battery supply 507 and a power switch 508.

PEAD 500 also includes a local area transceiver 509, such as but not limited to a 433 MHz transceiver, equipped with an antenna 510. Transciever 509 listens, using antenna 510, for signals x-mitted via sensor antenna(s) 5221, 522*b*, 522*m* from remote sensors 521*a*, 521*b*, 521*m* (collectively 521) (FIG. 13) located within the signal range of hub 500. In an embodiment, transceiver 509 (FIG. 13) is a receiver only, and only receives signals from the remote sensors 421 but does not transmit signals to the remote sensors 421. Such arrangement reduces the power required to power the remote sensors 521. In an embodiment, any number of remote sensors 521 may transmit alerts to the PEAD hub 500, and the PEAD hub 500 may process alerts sent by any number of remote sensors 521. In this way, PEAD hub 500 operates as a gateway between the remote sensors 521 and PEANS 300 for sending out alert notifications to notification recipients.

In an embodiment, transceiver 509 comprises a 433 MHz transceiver that listens for messages sent from remote sensor devices 521 (or, as discussed in connection with FIG. 15, PEADs 540) that are located within reception distance of the PEAD hub 500 (e.g., within approximately 100 meters). In an embodiment, to conserve power, the transceiver 509 activates or "wakes up" periodically to listen for a message from a remote sensor unit. In an embodiment, the transceiver 509 wakes up every second or few seconds to check for messages. In implementation, the remote sensors 521 or remote PEADs 541 may be configured to transmit for a few times longer than the transceiver wake period, so that the transceiver 509 is guaranteed to be in a wake period at least once during the sensor/PEAD alert signal transmission period. In order to conserve battery life, both the transceiver 509 of the PEAD hub 500 and the remote sensor(s) 521/remote PEADs 540 automatically go into a power saving mode state when not transmitting or when not in a wake period. Further to conserve power, the transceiver 509 and the components of the remote sensors 521/remote PEADs 540 are implemented using low-power electronic components.

Optionally, PEAD 500 itself may include one or more sensors 506a, 506b, 506n (collectively 506) that sense, and/or sense and process, one or more predefined conditions in the environment 520 and alert the controller 501 upon detection of such predefined condition(s). Sensors 506 may be directly electrically coupled to the controller 501. For example, each of sensors 506 may have a corresponding alert output that electrically connects, directly or indirectly through additional circuitry, to one or more interrupt ports of the controller 501. Corresponding interrupt service routines within the program code of the controller 501 (which may be stored in memory 502) implement control logic for processing the alert, decoding the alert (if necessary), determining whether to send an alert message to an external Notification Service (such as PEANS 300) in cooperation with the cellular modem 503 over a cellular network such as a low-power wide area network (LPWAN). In an embodiment, no sensors 506 exist on board the PEAD hub 500, as indicated by the dashed lines in FIG. 14. In an alternative embodiment, one or more sensors 506 are implemented on board the PEAD hub 500.

Figure 15:
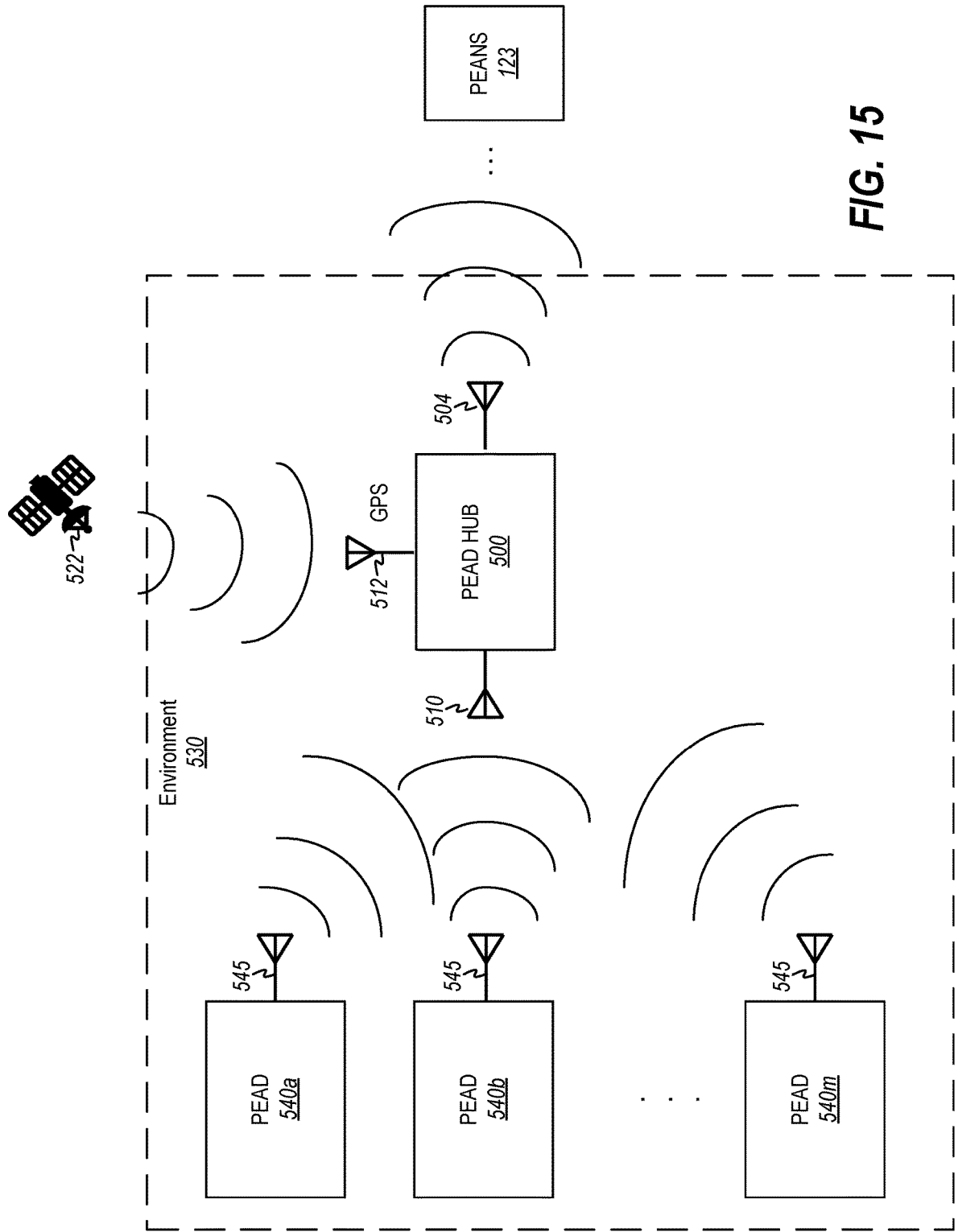
FIG. 15 is a system diagram illustrating a personal emergency alert device hub system in communication with remote personal emergency alert devices.
Figure 16:
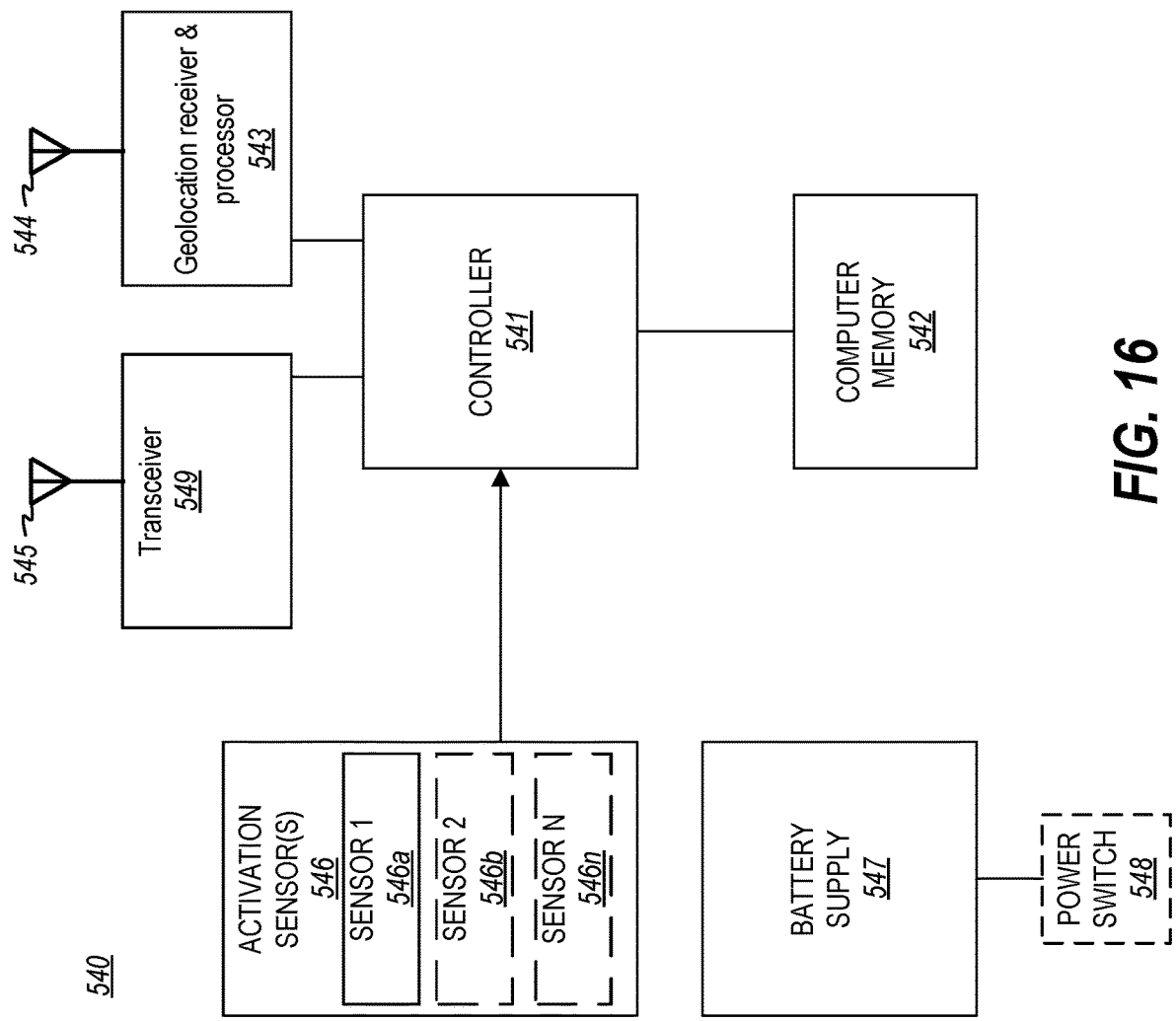
FIG. 16 is a block diagram illustrating an exemplary embodiment of a personal emergency alert device for use in the hub system of FIG. 15.

FIG. 15 illustrates another embodiment of a hub-based personal emergency alert device system in which individual PEADs 540a, 540b, 540m send alerts to a PEAD hub 500 rather than directly to the PEANS 123. Generally, the communications protocol between a PEAD 540a, 540b, 540m and the PEAD hub 500 is a mid-range protocol, such as 433 MHz, Zigbee, WiFi, etc., and PEADs 540a, 540b, 540m are positioned in the environment 530 within RF range of the PEAD hub 500. For 433 MHz transmission protocols, the range is approximately 100 meters. The PEAD hub 500 includes a local area antenna which receives signals from the remote PEADS 540a, 540b, 540m, processes the signals, and sends alert messages corresponding to alerts received from the remote PEADS 540a, 540b, 540m to the PEANS 123. FIG. 16 is a block diagram illustrating an exemplary embodiment of a PEAD 540 that may be used to implement PEADs 540a, 540b, 540m in the hub system of FIG. 15. As illustrated, PEAD 540 includes controller 541, memory 542, battery supply 547, power switch 548, local area transceiver 549 with local area antenna 510, and one or more activation sensor(s) 546a, 546b, 546n (collectively 546). PEAD 540 may also include a geolocation receiver and processer 543 to collect geolocation information to allow PEAD location tracking. The configuration and operation of PEAD 540 is similar to that of PEAD 500 discussed above in connection with FIG. 14, with the exception that transceiver 549 is implemented using a suitable technology to communicate with a PEAD hub 500 rather than directly to the cellular network 110. For example, transceiver 549 may be implemented using a 433 MHz modem, Zigbee, WiFi, or other shorter range and/or low power communications protocol.

Figure 17:
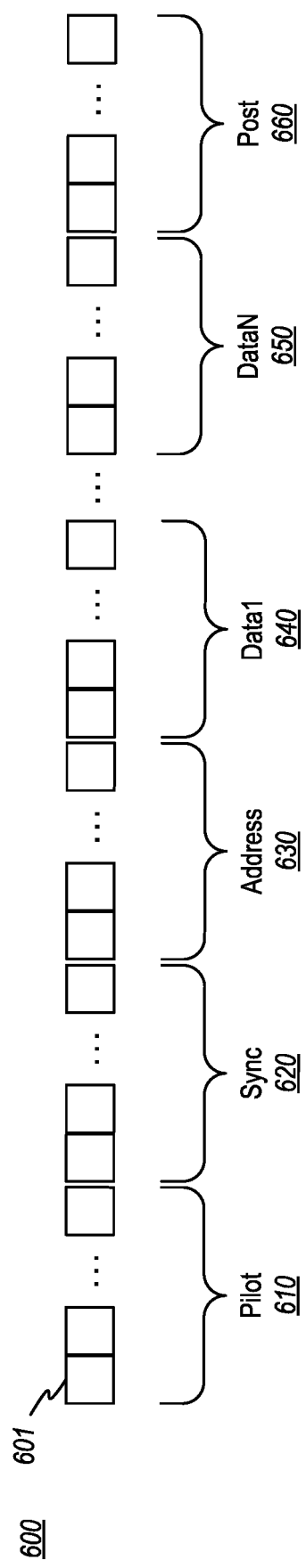
FIG. 17 is a data format diagram illustrating an exemplary embodiment of a data transmission packet.

FIG. 17 depicts an example high-level format of a message 600 that is transmitted either by a sensor 521a, 521b, 521m or a PEAD 540a, 540b, 540c to a PEAD hub 500. As illustrated, the message comprises a plurality of binary bits 601 arranged to form a plurality of fields 610, . . . , 660. Field 610 comprises a number of bits referred to as a pilot period which the transceiver 509 of PEAD hub 500 uses to trigger the start of a potential message. A synchronization period field 620 comprises a known pattern of bit values used by PEAD hub 500 to synchronize the transceiver 509 with the incoming data stream. Following the sync period, in an embodiment, the message 600 contains an address period field 630 containing an address recognizable by PEAD hub 500 to indicate it should process the message 600. Message 600 includes a number of data fields 640, . . . , 650, which contain at least sensor/PEAD identification data (such as serial number, the type of the sensor, and a number of status and/or control bits from which the controller 501 can identify which sensor is sending the message, and what its status is and/or whether it needs to perform any control operations (such as updating firmware, notifying of a low battery condition, etc.). The message 600 finally includes a Post field 660 which contains a code indicating the end of the message 600.

As discussed previously, any of the PEADs 20, 540 or PEAD hub 500 may include a geolocation module in order to track the location of the respective PEAD/hub. Such geolocation modules may be implemented with a Global Navigation Satellite System (GNSS) receiver (and processor) such as one capable of acquiring and processing signals from the Global Positioning System (GPS), GLONASS, Galileo, Beidou and other regional satellite navigation systems. The GNSS receiver determines a geolocation of the PEAD/hub using time signals transmitted from satellites 522 via satellite radio waves along a line of sight. In an embodiment, the GNSS receiver is integrated into the same integrated circuit chip as the cellular modem. For example, in embodiments where a PEAD 20 or hub 500 sends messages to PEANS over a cellular network 110 using a cellular modem, the cellular modem and GNSS Receiver may be implemented using a Quectel BG96, as detailed previously.

In embodiments, the respective controllers 21, 501, 541 of PEAD/hub 20, 500, 540 may turn on the GNSS receiver periodically to acquire the current position of the PEAD/hub 20, 500, 540. In embodiments, when an alert message is formulated and sent to PEANS 123, the PEAD/hub controller 21, 501, 541 obtains the current (or most recent) geo-spatial (also referred elsewhere herein as "geolocation") position of the PEAD/hub as acquired by the GNSS Receiver, and includes the current (or most recent) location coordinates in the payload of the alert message that it sends to PEANS 123. PEANS 123 may use the geo-spatial position coordinates as data input to its control logic. Alternatively, PEANS 123 may include the geo-spatial position coordinates in its message to notification recipients.

As previously mentioned, an important consideration in the implementation of the PEAD module or PEAD and other system elements may be the limited power supply available for powering the PEAD/hub due to its stand-alone battery power supply. In order to maximize the life of the PEAD/hub in the field, the PEAD/hub may be configured to implement several additional power saving features. In an embodiment, the PEAD/hub controller 21, 501, 541 is programmed to determine whether, and how often, to send an alert message to the PEANS 123 when a given activation sensor 26, 506, 521, 546 is triggered. For example, in an embodiment, a controller may be programmed to send an alert message to the PEANS every time such controller receives notification that a given sensor is triggered. However, for situations where the same sensor continuously triggers due to the same trigger condition over a certain period of time, repeated alert messages that provide no additional information may be generated. To conserve battery power, in an embodiment, such controller may be programmed not to send an alert message to PEANS 123 if it has already sent an alert message within a programmed amount of time. Such controller may further be programmed to change the rate at which it sends alert messages. For example, when such controller receives an alert message from a given activation sensor, it may immediately send an alert message to PEANS 123. Upon receipt of a second alert message gend by the same activation sensor within a given period of time from the first alert message, such controller may delay sending another alert message to PEANS 123 until a certain amount of time has passed and the condition still exists, and/or may gradually increase the delay in sending additional alert messages if it continues to receive alert signals that appear to be a result of the same condition.

Determination of whether to send an alert to PEANS 123 may vary depending on the purpose and application of use of the PEAD/hub 20, 540, 500. In an embodiment, a PEAD/hub controller sends an alert message for every alert generated by an activations sensor. In an embodiment, such controller sends an alert upon the satisfaction of one or more additional conditions (for example, a certain amount of time must pass before sending a next alert). In an embodiment, once an alert is sent, if the sensed condition continues without cease for a certain duration of time, the controller sends only one or a small few alerts. If the sensed condition ceases, in an embodiment, the controller may send another alert indicating cessation of the sensed condition. In general, the controller may be programmed to send as many or few alert messages to the PEANS as meets the requirements of the application and purpose for which the PEAD system is installed. For example, it may be sufficient to alert the PEANS only once upon receipt of a first alert by an activation sensor and then ignore further alerts. In a different application, it may be better to require a set number of alerts from a given activation sensor before alerting the PEANS. In yet another application, it may be desired, once an alert message has been sent to the PEANS, to send an alert upon cessation of the condition that caused the alert. In accordance with the invention, many different scenarios in the alerting scheme are feasible and contemplated for use with the PEAD, and any exemplary embodiments described herein are not intended to be limiting.

In an embodiment, upon receiving an alert message, the PEANS decodes the alert and extracts the device identifier and alert code and/or other message information from the alert message. Depending on the specific alert code and/or other message information, the PEANS may determine whether to send a notification message to the notification recipients associated with the PEAD/hub. In an embodiment, the PEANS sends a notification message to all notification recipients for every alert message it receives from the PEAD/hub. In an alternative embodiment, the PEANS may process the alert code and send a notification message only under certain conditions. For example, if the PEANS determines it has received an identical alert code within a predetermined time period before the receipt of the present alert code, it may be programmed to ignore the later-received alert message from the PEAD/hub until the predetermined time period has passed. Alternatively, the PEANS may continue to send alert notification messages to the notification recipient(s) upon receipt of repeat alert notifications from the PEAD/hub, but the controller may increase, or gradually increase, the time between sending notification messages to the notification recipients. In this way, notification recipients will not be overwhelmed with notification messages that alert to the same ongoing condition.

It will be appreciated that personal emergency alert systems and technologies, in particular the PEAD, PEAD hub and Notification Service (PEANS), may be implemented and used to alert and notify of many diffrt types of personal emergencies. By way of example and not limitation, in an embodiment, an activation sensor, and the basis on which a personal emergency alert condition may be based, may comprise one, or a combination of, the following sensors: an accelerometer, a microphone, a passive infrared (PIR) sensor, a reed switch, a camera, a liquid level sensor, a charge sensor, a load sensor, a voltage sensor, a resistance sensor, a capacitance sensor, a thermo sensor, a temperature sensor, a humidity sensor, a flex sensor, a pressure sensor, a chemical composition sensor, a light sensor, a UV Index sensor, a sound sensor, a wind sensor, a positioning sensor, a moisture sensor, etc. In an embodiment, such as discussed in connection with FIGS. 13 and 14, a system includes a plurality of sensor units positioned in proximity (within receiver range) to the transceiver of a PEAD. Such PEAD includes program instructions to listen for sensor event alerts from sensor units 521 within its receiving range, identify the sensor sending a sensor event alert, decode such sensor event alert(s) and send one or more message alert(s) to the PEANS to alert notification recipients to the occurrence of the sensor event corresponding to a personal emergency using one of the designated notification delivery methods associated with the PEAD/PEAD hub.

The mapping service discussed in connection with FIG. 9 may also be used to generate a map for display on a notification recipient's device 5. Locations of individual sensors 406 and the PEAD may be overlaid on a map.

Another advantage of the systems discussed herein, and in particular with respect to the PEAD system with external sensors as discussed in connection with FIGS. 13-14 is that it allows end users to set up a personal emergency monitoring and notification system on a modular basis. That is, an end user can install a PEAD hub in an environment, and then place remote sensor units 521 of the same or different types, or may place local PEADs 540, anywhere within the signal range of the PEAD hub 500, and receive alerts if any one of the remote sensors detect a condition that corresponds to a personal emergency event. The placement of the sensors 521 is completely up to the end user, and no sensor 521a, 521b, ..., 521m is required to communicate with any other sensor in the system. Each individual sensor 521 need only transmit an alert using the sensor transceiver protocol that is recognized by the PEAD hub 500, and the PEAD hub 500 will pick up the alert and notify the PEANS to notify the notification recipients associated with the PEAD/PEAD hub. The modular personal emergency monitoring system is easy to install because, since the PEAD/sensors/hub each is equipped with a self-contained power source (i.e., a battery or solar panel/inverter) and does not require a WiFi or LAN access port, the PEAD hub and sensors/PEADs can be placed anywhere with range of the PEAD hub, including remote locations so long as the LPWAN provides sufficient coverage to allow the PEAD hub to connect to the LPWAN. The advantages of the novel personal emergency alert system over existing and prior art monitoring and notification systems are many: the personal emergency alert devices and/or sensors are modular, the system is a Do-It-Yourself, simple to install and user-configurable monitoring system design, once activated, geolocation tracking is always on (until power runs out), the PEAD either cannot be switched off or can only be turned off by an independent source using a secure protocol, and the hardware is long-lasting and self-contained.

It will further be appreciated that although the preferred embodiment uses an LPWAN over which to transmit alert messages, in other embodiments, the PEAD module and/or PEAD may additionally or instead be equipped with a WiFi modem to transmit the messages to the nearest WiFi access port and from there onto the Internet to the Notification Service.

PEAD Housing and/or Integration with Other Items

Figure 18:
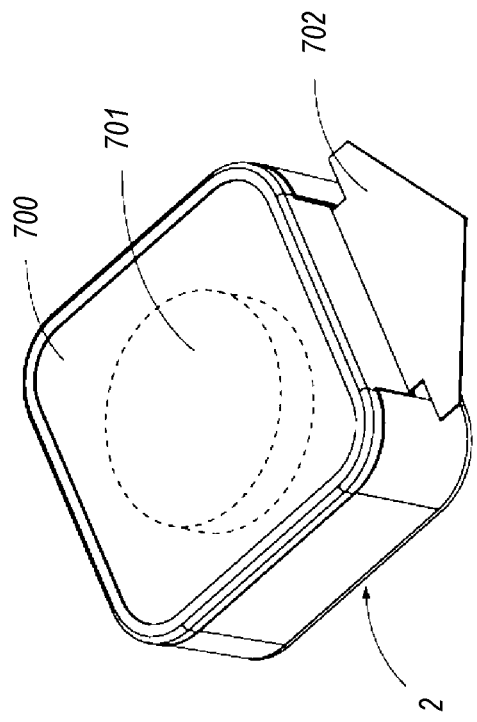
FIG. 18 is a perspective view of an embodiment of a push-button personal emergency alert device.

FIG. 18 depicts an example embodiment of a personal emergency alert device 2 housed in a housing 700. In the depicted embodiment, the personal emergency alert device 2 is powered by battery 701 and is powered on by pulling an insulating pull-tab 702 to connect the battery 701 to the internal circuitry of the personal emergency alert device 2. Once powered on, personal emergency alert device 2 follows the method described in connection with FIG. 3A.

In an embodiment, the insulating pull-bat 702 is the method of activation, and once removed, the PEAD 2 begins alert transmission(s). While not shown, personal emergency alert device 2 may also include a push-button switch and may be designed such that once the PEAD 2 is turned on (for example, by removing the pull-tab 702), a user requiring emergency assistance need only push the push-button switch to generate the activate the PEAD to send an alert message to the personal emergency alert notification service (PEANS) and start tracking the geolocation of the device 2.

In certain situations the PEAD 2 is most effective for its purpose if its presence and location is easily noticed and/or known by the user(s) it is intended to serve. For example, a PEAD 2 may be installed in living environment of people who may require more attentive care (including independent living environments, nursing homes, assisted living environments), in hospitals, office buildings, public buildings, day care centers, community centers, prisons, elevators, trains, public/private transport vehicles, etc.), When used for such situations, the housing 700 of the PEAD 2 is preferably conspicuous so that the user 4a or other people who are requesting assistance on the user's behalf easily notice the presence and location of the PEAD 2. Housing 700 (i.e., the package or container that the electronics of the PEAD 2 are contained within) may be made conspicuous through one or more, or a combination of, housing size, color, lighting, signage, etc. Additionally, such situations may call for a very simple user interface. In an embodiment, the user interface is a simple push button to activate the device.

Other situations may call for less conspicuous PEAD housing 700. For example, when the PEAD 2 is used as an emergency call device by people who may be more vulnerable circumstances (e.g., elderly people living independently), the PEAD 2 may be worn on the user's person such as a necklace or bracelet (see personal emergency alert device 2 on user 4a in FIG. 1), on a strap attached to the person's clothing, etc. Accordingly, the housing of the PEAD 2 may be made to be less conspicuous in terms of its size, color and design. In still other situations, it may be desirable to incorporate the PEAD 2 into clothing, accessories, and/or everyday items so as to be inconspicuous or even disguised or hidden. Situations that may call for a PEAD that is inconspicuous, disguised or hidden may include, without limitation, situations where the user 4a is alone or with unknown people, or may encounter a compromising situation, or there is concern for the user's safety. In embodiments, the PEAD 2 may be incorporated into wearable items, such as clothing, earrings, necklaces, watches, shoes, shoestrings, eyeglasses, hair clips, and/or other accessories. PEAD 2 may also be incorporated into everyday items such as a handbag, wallet, mobile phone, phone case, eyeglasses case, cosmetic case, and so on.

Those of skill in the art will appreciate that aspects of the invented device, system and methods described and illustrated herein may be implemented in software, firmware or hardware, or any suitable combination thereof, including by way of a computer or microprocessor process in which instructions are executed, the instructions being stored for execution on a computer-readable medium and being executed by any suitable instruction-processing CPU, microprocessor, FPGA, or other hardware. Alternative embodiments are contemplated, however, and are within the spirit and scope of the invention.

What is claimed is:

1. A personal emergency alert notification method executed by a personal emergency alert device maintained in accessible proximity to a user, the device comprising a cellular modem, a geolocation module, and a sensor, the device powered by a power source when placed in a power-on mode, the method comprising the steps of:
   generating, by the sensor, an activation signal upon detection of an activation event;
   in response to the activation signal:
      obtaining, by the geolocation module, geolocation data indicative of a geolocation of the device;
      formulating an alert message comprising geolocation information indicative of the geolocation of the device, the geolocation information based on the geolocation data;
      transmitting, by the cellular modem, the alert message to a remote cellular-enabled receiver configured to receive and send that alert message to a personal emergency alert notification service executing on a remote computer and accessible through a packet data network;
   repeating steps of obtaining, formulating, and transmitting, wherein the repeating is halted only upon occurrence of a deactivation event comprising receiving, by the device, a deactivation code from a personal alert notification service, wherein the personal alert notification service performs the steps of:
      receiving, by a source other than the device, a deactivation message;
      extracting a deactivation code from the deactivation message;
      determining whether the deactivation code is valid;
      determining whether the valid deactivation code comprises a true emergency code or a true deactivation code;
      only transmitting the valid deactivation code to the device if the valid deactivation code comprises the true deactivation code; and
      halting, by the device, the repeating upon receipt of the valid deactivation code.

2. The method of claim 1, wherein the sensor comprises a power-on switch and the activation event comprises setting the power-on switch to place the device into the power-on mode.

3. The method of claim 1, wherein the sensor comprises a push-button switch and the activation event comprises pressing the push-button switch.

4. The method of claim 1, wherein the sensor comprises a switch and the activation event comprises setting the switch to a predetermined state.

5. The method of claim 1, wherein the sensor comprises a microphone and a signal processor, and the activation event comprises detecting a match between a predetermined trigger signature and a signature generated by the signal processor based on sound detected by the microphone.

6. The method of claim 1, wherein the sensor comprises an environmental condition sensor and the activation event comprises occurrence of a predetermined environmental condition.

7. The method of claim 1, further comprising:
the personal emergency alert notification service receiving the alert, determining one or more notification recipients associated with the device, and transmitting an emergency alert message to the one or more notification recipients via one or more of an SMS text message, an email message, or an Internet-enabled message delivery service.

8. The method of claim 1, wherein the power source comprises a battery supply embedded within the device, and wherein the deactivation event further comprises depletion of the power source below a power level sufficient to operate the device.

9. The method of claim 1, further comprising:
between successive execution of the repeating step:
placing the device into a low power mode comprising turning off, or placing in a low power state, selected high-power consumption features of components of the device;
delaying for a predetermined time interval; and
upon expiration of the predetermined time interval, exiting the low power mode by turning on, or exiting from the low power state of, the selected high-power consumption features of the components of the device.

10. The method of claim 9, further comprising:
prior to the detection of the activation event, placing the device into the low power mode; and
in response to the activation signal resulting from the detection of the activation event, exiting the low power mode.

11. The method of claim 10, wherein the transmitting step comprises transmitting the alert message over a low power wide area network (LPWAN).

12. The method of claim 11, wherein the LPWAN comprises a Long Term Evolution (LTE) network.

13. The method of claim 12, wherein the alert message is transmitted according to a protocol in accordance with a Long Term Evolution (LTE) CAT-M1 protocol or a LTE Narrow-Band Internet-of-Things (NBIoT) protocol.

14. The method of claim 9, wherein:
in response to placement of the device into the power-on mode, instructing the cellular modem to establish radio access network bearers to create a data tunnel between the device and a packet data network through which the device can access the personal emergency alert notification service; and
maintaining the established radio access network bearers as long as the device is in the power-on mode.

15. The method of claim 14, further comprising:
prior to the detection of the activation event, placing the device into the low power mode; and
in response to the activation signal resulting from the detection of the activation event, exiting the low power mode.

16. A personal emergency alert device comprising:
a cellular modem;
a geolocation module arranged to obtain geolocation information representative of a geolocation of the device;
a sensor arranged to detect an activation event and to generate an activation signal upon detection of the activation event;
a controller in electrical communication with the sensor, the cellular modem, and the geolocation module;
a power switch that switchably connects a power source to the controller, the sensor, the cellular modem, and the geolocation module to place the device into a power-on state;
wherein:
the controller, responsive to placement of the device into the power-on state, instructs the cellular modem to establish radio access network bearers to create a data tunnel between the device and a packet data network through which the device can communicate with a personal emergency alert notification service that is accessible via the packet data network, and
the controller, responsive to the activation signal, repeatedly performs an operation of (a) instructing the geolocation module to obtain the geolocation information, (b) formulating an alert message comprising the obtained geolocation information, and (c) instructing the cellular modem to transmit the alert message to the personal emergency alert notification service via the data tunnel, the controller halting the repeated performance of the operation only upon occurrence of a deactivation event comprising receipt by the device of a valid deactivation code from a source other than the device;
wherein the controller is configured to receive a deactivation code from a personal alert notification service, wherein the personal alert notification service is configured to:
receive, by a source other than the device, a deactivation message;
extract a deactivation code from the deactivation message;
determine whether the deactivation code is valid and whether the valid deactivation code comprises a true emergency code or a true deactivation code;
only transmitting the valid deactivation code to the device if the valid deactivation code comprises the true deactivation code; and
wherein the controller is configured to halt he repeated performance of the operation upon receipt of the valid deactivation code.

17. The device of claim 16, wherein the geolocation module comprises a Global Positioning System (GPS) transceiver.

18. The device of claim 16, wherein the sensor comprises the power switch and the activation event comprises placement of the power switch into the power-on state.

19. The device of claim 16, wherein the sensor comprises a microphone and a signal processor, and the activation event comprises detecting a match between a predetermined trigger signature and a signature generated by the signal processor based on sound detected by the microphone.

20. The device of claim 16, wherein the sensor comprises an environmental condition sensor and the activation event comprises occurrence of a predetermined environmental condition.

21. The device of claim 16, wherein the controller, between each performance of the repeated operation:
places the device into a low power mode comprising turning off, or placing in a low power state, selected high-power consumption features of the geolocation module, the cellular modem and/or the controller;
delays for a predetermined time interval; and
upon expiration of the predetermined time interval, exits from the low power mode by turning on, or exiting from the low power state of, the selected high-power consumption features of the geolocation module, the cellular modem and/or the controller.

22. The device of claim 21, wherein the controller, prior to the detection of the activation event, places the device into the low power mode, and instructs the device to exit the low power mode in response to the activation signal resulting from the detection of the activation event.

23. The device of claim 21, wherein the established radio access network bearers are maintained throughout the duration of the device being in the power-on mode.

24. The device of claim 23, wherein:
the controller, after instructing the cellular modem to establish the radio access bearers and in the absence of yet receiving the activation event, placing the device into the low power mode, and instructs the device to exit from the low power mode upon receiving the activation event.

25. The device of claim 21, wherein the transmitting step comprises transmitting the alert message via the radio access network bearers to the data packet network over a low power wide area network (LPWAN).

26. The device of claim 25, wherein the LPWAN comprises a Long Term Evolution (LTE) network.

27. The device of claim 26, wherein the alert message is transmitted according to a protocol in accordance with Long Term Evolution (LTE) Category-M1 (CAT-M1) protocol or an LTE Narrow-Band Internet-of-Things (NBIoT) protocol.

28. The device of claim 19, wherein the deactivation event further comprises receipt by the device of a deactivation code, and wherein the controller, responsive to receipt by the cellular modem of a deactivation code from a source other than the device, determines whether the received deactivation code is valid and halts the repeated performance of the operation if the received deactivation code is determined to be valid.

* * * * *